(12) United States Patent
Parikh et al.

(10) Patent No.: US 12,220,486 B2
(45) Date of Patent: Feb. 11, 2025

(54) POLYMER COMPOSITIONS FOR STORAGE AND RELEASE OF POLYPEPTIDES

(71) Applicant: Saint Joseph's University, Philadelphia, PA (US)

(72) Inventors: Vaishnavi Parikh, Sellersville, PA (US); Pardeep Gupta, West Chester, PA (US)

(73) Assignee: Saint Joseph's University, Philadelphia, PA (US)

( * ) Notice: Subject to any disclaimer, the term of this patent is extended or adjusted under 35 U.S.C. 154(b) by 0 days.

(21) Appl. No.: 16/977,222

(22) PCT Filed: Mar. 2, 2019

(86) PCT No.: PCT/US2019/020453
§ 371 (c)(1),
(2) Date: Sep. 1, 2020

(87) PCT Pub. No.: WO2019/169370
PCT Pub. Date: Sep. 6, 2019

(65) Prior Publication Data
US 2021/0154144 A1    May 27, 2021

Related U.S. Application Data

(60) Provisional application No. 62/637,906, filed on Mar. 2, 2018.

(51) Int. Cl.
| | |
|---|---|
| *A61K 9/14* | (2006.01) |
| *A61K 38/17* | (2006.01) |
| *A61K 38/27* | (2006.01) |
| *A61K 47/34* | (2017.01) |

(52) U.S. Cl.
CPC .............. *A61K 9/146* (2013.01); *A61K 38/27* (2013.01)

(58) Field of Classification Search
CPC ................................ A61K 9/146; A61K 38/27
See application file for complete search history.

(56) References Cited

U.S. PATENT DOCUMENTS

| | | | |
|---|---|---|---|
| 2002/0136776 A1 | 9/2002 | Fang et al. | |
| 2003/0049298 A1 | 3/2003 | Ohagan et al. | |
| 2003/0125237 A1* | 7/2003 | Kim | A61P 5/50 424/46 |
| 2003/0129233 A1 | 7/2003 | Vook et al. | |
| 2005/0220883 A1 | 10/2005 | Ohagan et al. | |
| 2007/0116709 A1 | 5/2007 | Ohagan et al. | |
| 2009/0011004 A1* | 1/2009 | Lutz | B82Y 5/00 435/375 |
| 2011/0172141 A1 | 7/2011 | Naylor et al. | |
| 2016/0129133 A1* | 5/2016 | McCreedy | A61K 47/6937 424/179.1 |
| 2017/0065523 A1* | 3/2017 | Nguyen | A61K 31/5377 |
| 2017/0319505 A1* | 11/2017 | Williams | A61K 38/19 |

FOREIGN PATENT DOCUMENTS

| | | | |
|---|---|---|---|
| WO | 2014/033346 | * | 3/2014 |
| WO | 2015126234 A1 | | 8/2015 |

OTHER PUBLICATIONS

Tsai, et al., "Adsorption of peptides to poly(D,L-lactide-co-glycolide): 1. Effect of physical factors on the adsorption", Intl J Pharma, vol. 127, Issue 1, Jan. 15, 1996, pp. 31-42.
Shah, et al., "Structural Stability of Recombinant Human Growth Hormone (r-hGH) as a Function of Polymer Surface Properties", Pharm Res, vol. 35, No. 98, pp. 1-18, Mar. 15, 2018.
International Search Report and Written Opinion dated May 15, 2019 for corresponding International Application No. PCT/US2019/020453.
Taluja, et al., "Novel approaches in microparticulate PLGA delivery systems encapsulating proteins", J Mater Chem, 17, Aug. 14, 2007, pp. 4002-4014.

* cited by examiner

*Primary Examiner* — Brian Gulledge
(74) *Attorney, Agent, or Firm* — Saul Ewing LLP; Domingos J. Silva; Chihao Wang

(57) ABSTRACT

The present invention relates to the discovery of novel PLGA particles comprising a polypeptide adsorbed on the surface of the PLGA particles. In certain embodiments, the PLGA particles can be used to administer the polypeptide to a patient in need thereof. As compared to polypeptide-delivery formulations known in the art, the present invention demonstrates a higher relative polypeptide loading capacity. In certain embodiments, the polypeptide adsorbed on the surface of the PLGA nanoparticles does not denature or deform upon adsorption.

17 Claims, 22 Drawing Sheets r-hGH: Dh = 4.8 ± 0.6 nm, PLGA: Dh = 50.2 ± 0.3 nm r-hGH: Dh = 4.3 ± 0.5 nm, PLGA: Dh = 50.1 ± 0.1 nm r-hGH: Dh = 4.9 ± 0.9 nm, PLGA: Dh = 50.9 ± 0.1 nm r-hGH: Dh = 4.8 ± 0.6 nm, PLGA: Dh = 79.6 ± 0.6 nm r-hGH: Dh = 4.3 ± 0.5 nm, PLGA: Dh = 80.8 ± 0.4 nm r-hGH: Dh = 4.8 ± 0.6 nm, PLGA: Dh = 48.2 ± 0.05 nm r-hGH: Dh = 4.3 ± 0.5 nm, PLGA: Dh = 48.7 ± 0.58 nm

POLYMER COMPOSITIONS FOR STORAGE AND RELEASE OF POLYPEPTIDES

CROSS-REFERENCE TO RELATED APPLICATIONS

The present application is a 35 U.S.C. § 371 national phase application from, and claims priority to, PCT International Patent Application No. PCT/US2019/020453, filed Mar. 2, 2019, which claims priority under 35 U.S.C. § 119(e) to U.S. Provisional Application No. 62/637,906, filed Mar. 2, 2018, all of which are hereby incorporated by reference herein in their entireties.

BACKGROUND OF THE INVENTION

An important factor in the selection of a polymer for protein delivery is the adsorption of proteins at solid/liquid interface of the polymer, as proteins may become unstable due to interactions with the solid surface of the polymer. Most protein-particle interactions occur at specific regions of proteins through hydrophobic or electrostatic interactions. In addition, denaturation of the protein due to adsorption onto solid surfaces, leading to loss of therapeutic activity and potential for toxicity and immunogenicity, has been documented.

When it comes to administration of recombinant human growth hormone (r-hGH), short half-life, instability in gastrointestinal tract, and low plasma circulation time requiring frequent parenteral administration can lead to patient non-compliance. One approach to remedying these issues focuses on prolonging the half-life of the protein drug through the use of biodegradable polymer microspheres.

Interaction of r-hGH with protein coated surfaces and non-biodegradable polymer surfaces such as silica particles, polystyrene particles, and other hydrophilic and hydrophobic surfaces have been previously investigated. Adsorption behavior of r-hGH on self-assembled monolayers (SAMs) prepared from octadecyltrichlorosilane (OTS), arachidic acid (ArAc), and dipalmitoylphosphatidylcholine (DPPC) has been studied and compared to adsorption behavior on silica and methylated silica surfaces. These studies revealed that adsorption on methylated surfaces results in a relatively large conformational change in the growth hormone's structure. These studies showed that the adsorption is considerably larger for alkylated surfaces with ordered alkyl chains in comparison to those with less ordered alkyl chains. Adsorption of r-hGH onto positively ($PS^+$) and negatively ($PS^-$) charged polystyrene nanoparticles was found to be irreversible with respect to dilution (less than 15% desorbed after 48 hours) for most pH conditions studied. Desorption occurred for r-hGH adsorbed onto $PS^-$ at pH 7.2 (45%) and onto $PS^-$ (18%) and $PS^+$ (34%) at pH 5.3. Additionally, these studies showed significant-conformational changes for r-hGH adsorbed onto $PS^+$ at all pH values and at certain pH values for $PS^-$. Other studies demonstrated that PLGA microspheres of r-hGH, prepared with zinc oxide and hydroxypropyl-β-cyclodextrin as the release modulator, afforded sustained release for 14 days in rats and 28 days in monkeys, but the composition had a limited loading amount of 13%±3% and demonstrated a low bioavailability of r-hGH (21% in rats and 30-49% in monkeys).

There remains a need in the art for novel compositions and methods for delivering polypeptides in vivo. In certain embodiments, such compositions should comprise a medium capable of stabilizing and transporting the polypeptide in biological conditions at high loading and without denaturing the polypeptide. The present invention meets these needs.

BRIEF SUMMARY OF THE INVENTION

In one aspect, the invention provides a method of forming polypeptide-adsorbed poly (lact poly(lactic-co-glycolic acid) (PLGA) particles. The method includes contacting an aqueous suspension comprising PLGA particles with an aqueous solution comprising the polypeptide. In another aspect, the invention provides a composition comprising polypeptide-adsorbed PLGA particles formed through any of the methods of the invention. In another aspect, the invention provides a composition comprising polypeptide-adsorbed PLGA particles. In yet another aspect, the invention provides a method of treating human growth hormone deficiency in a subject in need thereof. In yet another aspect, the invention provides a method of delivering a polypeptide to the lungs of a subject in need thereof.

In certain embodiments, the PLGA particles comprise nanoparticles having a diameter of about 1 nm to about 100 nm. In certain embodiments, the PLGA particles comprise microparticles having a size of about 0.5 μm to about 5 μm. In certain embodiments, the PLGA particles comprise porous microparticles having diameter of about 10 μm to about 20 μm and an aerodynamic diameter of about 0.5 μm to about 5 μm.

In certain embodiments, the aqueous solution comprises about 0.001 mg/ml to about 0.2 mg/ml the polypeptide. In certain embodiments, the polypeptide is selected from the group consisting of a monoclonal antibody, coagulation factor, enzyme, fusion protein, hormone, growth factor, and plasma protein. In certain embodiments, the polypeptide is a recombinant polypeptide. In certain embodiments, the polypeptide is selected from the group consisting of human growth hormone (hGH), insulin, somatostatin analogue, recombinant human glucocerebrosidase, vasopressin, leuprolide acetate, goserelin acetate, triptorelin, GLP-I receptor agonist, coagulation factor IX, recombinant factor VIII.

In certain embodiments, the aqueous suspension has a pH of about 6.5 to about 7.5. In certain embodiments, the aqueous solution has a pH of about 6.5 to about 7.5.

In certain embodiments, the PLGA particles comprise a lactic acid/glycolic acid ratio from about 1:1 to about 6:1.

In certain embodiments, the PLGA particles comprise PLGA 5050 or PLGA 8515. In certain embodiments, the PLGA particles comprise a PLGA polymer having a molecular weight from about 10 kDa to about 50 kDa. In certain embodiments, at least a portion of the PLGA particles comprise ester an end-capped PLGA polymer.

In certain embodiments, the aqueous suspension is buffered. In certain embodiments, the aqueous solution is buffered.

In certain embodiments, at least a portion of the polypeptide adsorbed to the surface of the PLGA particles retains its active secondary and tertiary structure as compared to the free non-adsorbed polypeptide. In certain embodiments, at least a portion of the polypeptide adsorbed to the surface of the PLGA particles is not significantly denatured by the adsorption process. In certain embodiments, the polypeptide adsorbs to the surface of the PLGA particles to form a monolayer. In certain other embodiments, the polypeptide adsorbs to the surface of the PLGA particles to form more than one layer.

In certain embodiments, the polypeptide is not imbedded in the PLGA particles.

In certain embodiments, the composition comprises a (w/w) ratio of the polypeptide:PLGA of about 1:0.15 to about 1:6.

In certain embodiments, the PLGA particles are biocompatible. In certain embodiments, the PLGA particles are biodegradable. In certain embodiments, the composition comprises at least one pharmaceutically acceptable carrier.

In certain embodiments, the subject is a mammal. In certain embodiments, the mammal is a human.

BRIEF DESCRIPTION OF THE FIGURES

For the purpose of illustrating the invention, depicted in the drawings are certain embodiments of the invention. However, the invention is not limited to the precise arrangements and instrumentalities of the embodiments depicted in the drawings.

DETAILED DESCRIPTION OF THE INVENTION

Figure 1A:
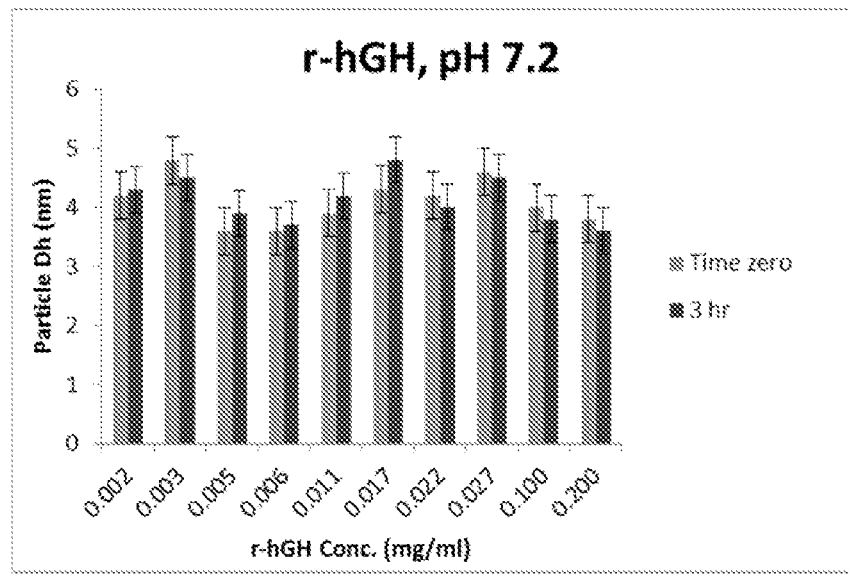
FIGS. 1A-1C are a set of graphs illustrating measurements at pH 7.2 (FIG. 1A), pH 5.3 (FIG. 1B), and pH 4.0 (FIG. 1C), using dynamic light scattering, of hydrodynamic diameter, Dh (nm) of r-hGH as a function of concentration of r-hGH (mg/ml) at 10 mM ionic strength of the solution at time zero and at 3 hour.

The present invention relates to the discovery of novel PLGA nanoparticles comprising polypeptides adsorbed on the surface of the PLGA nanoparticles. In certain embodiments, the polypeptide adsorbed on the surface of the PLGA nanoparticles does not significantly denature or deform upon adsorption. In certain embodiments, the novel PLGA nanoparticles can be used to administer hGH to a patient in need thereof. As compared to hGH delivery formulations known in the art, the present invention demonstrates a higher hGH loading capacity. In other embodiments, the novel PLGA nanoparticles can be used to administer polypeptides to the lungs of the a subject so as to treat a lung disease and/or a respiratory disease.

Compositions

In one aspect, the invention provides a composition comprising poly(lactic-co-glycolic acid) (PLGA) particles and a polypeptide, wherein the polypeptide is adsorbed on the surface of the PLGA particles.

In certain embodiments, the PLGA particles comprise microparticles having a size of about 0.5 µm to about 5 µm. In other embodiments, the PLGA particles comprise porous microparticles having diameter of about 10 µm to about 20 µm as well as an aerodynamic diameter of about 0.5 µm to about 5 µm.

In certain embodiments, the PLGA particles comprise nanospheres or nanoparticles. In yet other embodiments, the PLGA particles have a diameter of about 1 nm to about 1 µm. In yet other embodiments, the PLGA particles have a diameter of about 1 nm to about 100 nm.

In certain embodiments, the polypeptide is selected from the group consisting of a monoclonal antibody, coagulation factor, enzyme, fusion protein, hormone, growth factor, and plasma protein. In certain embodiments, the polypeptide is selected from the group consisting of human growth hormone (hGH), insulin, somatostatin analogue, recombinant human glucocerebrosidase, vasopressin, leuprolide acetate, goserelin acetate, triptorelin, GLP-I receptor agonist, coagulation factor IX, recombinant factor VIII. In certain embodiments, the polypeptide is a recombinant polypeptide.

In certain embodiments, the PLGA particles comprise a lactic acid to glycolic acid ratio from about 1:1 to about 6:1. In other embodiments, the PLGA particles are PLGA 5050 or PLGA 8515.

In certain embodiments, the PLGA particles comprise an ester end-capped PLGA polymer, wherein the polymer acid termini are at least partially esterified. In other embodiments, the PLGA particles do not comprise an ester end-capped PLGA polymer.

In certain embodiments, the PLGA particles comprise PLGA polymers having a molecular weight from about 10 kDa to about 100 kDa. In other embodiments, the PLGA particles comprise PLGA polymers having a molecular weight from about 10 kDa to about 50 kDa.

In certain embodiments, the PLGA particles are essentially fully coated with the polypeptide. In other embodiments, the PLGA particles are at least partially coated with the polypeptide. In yet other embodiments, at least a portion of the polypeptide adsorbed to the surface of the PLGA particles retains its active secondary and/or tertiary structure. In yet other embodiments, at least a portion of the polypeptide adsorbed to the surface of the PLGA particles is not denatured by the adsorption process. In yet other embodiments, essentially all of the polypeptide adsorbed to the surface of the PLGA particles is not denatured by the adsorption process.

In certain embodiments, the polypeptide adsorbs to the surface of the PLGA particles to form a monolayer. In other embodiments, the polypeptide adsorbs to the surface of the PLGA particles to form more than one layer (i.e. a multilayer). In yet other embodiments, the polypeptide is not imbedded in the PLGA particles.

In certain embodiments, the composition comprises a (w/w) ratio of the polypeptide:PLGA of about 1:0.15 to about 1:6.

In certain embodiments, the composition is a pharmaceutically acceptable composition. In other embodiments, the composition further comprises at least one pharmaceutically acceptable carrier.

In certain embodiments, the PLGA particles of the invention are biocompatible. In certain embodiments the particles of the invention are biodegradable In another aspect, the invention provides a method of making any of the compositions of the invention. In certain embodiments the method comprises contacting the polypeptide with an aqueous suspension comprising PLGA particles. In certain embodiments, the aqueous suspension is a buffered aqueous solution. In yet other embodiments, the buffered aqueous solution comprises at least one buffer selected from the group consisting of acetic acid and 2-ethanesulfonic acid. In other embodiments, the aqueous suspension is a buffered aqueous solution having a pH of about 4 to about 8. In yet other embodiments, the aqueous suspension has a pH of about 6.5 to about 7.5. In yet other embodiments, the aqueous suspension has a pH of about 7.2.

In certain embodiments, the method comprises contacting an aqueous suspension comprising PLGA particles with an aqueous solution comprising the polypeptide. In other embodiments, the aqueous solution comprises about 0.001 mg/ml to about 0.2 mg/ml of the polypeptide. In certain embodiments, the aqueous solution is a buffered aqueous solution. In yet other embodiments, the buffered aqueous solution comprises at least one buffer selected from the group consisting of acetic acid and 2-ethanesulfonic acid. In other embodiments, the buffered aqueous solution has a pH of about 4 to about 8. In yet other embodiments, the buffered aqueous solution has a pH of about 6.5 to about 7.5. In yet other embodiments, the buffered aqueous solution has a pH of about 7.2.

In certain embodiments, the PLGA particles are made by a nanoparticle precipitation method. In certain embodiments, the method comprises dissolving PLGA polymer in an organic solvent. In certain embodiments, the method comprises contacting the organic solvent comprising PLGA polymer with an aqueous solution. In certain embodiments, the method comprises stirring the solution to form a PLGA nanoparticle precipitate. In certain embodiments, the method comprises isolating the PLGA nanoparticle precipitate.

In certain embodiments, the PLGA microparticles are fabricated either through emulsion solvent evaporation or spray drying method. In certain embodiments, control of the size of the microparticles is achieved through the selection of certain parameters including polymer starting material, concentration of the polymer solution and aqueous phase stabilizers, aqueous to organic phase ratio, and homogenization speed.

In certain embodiments, the porous PLGA microparticles are fabricated with the use of a pore-former, which creates channels within the microparticles. In certain embodiments, the pore-former is added to a PLGA formulation and channels are created either as and when the microparticles harden, or when the pore-formers are extracted following the microparticle's hardening. In certain embodiments, the pore-former is selected from the group consisting of Pluronic F127, ammonium bicarbonate, sodium oleate, and oil. In an exemplary embodiment, the PLGA and Pluronic F127 are dissolved in an organic phase using dichloromethane (DCM). Subsequently, the organic phase having PLGA and Pluronic F127 is added to an aqueous phase, which is a polyvinyl alcohol (PVA) solution, under a high-speed stirring to create an emulsion. As the microparticles harden, the Pluronic F127 is extracted into the aqueous phase, consequently leaving behind the channels and the pores.

In certain embodiments, the method of making the composition of the invention comprises dissolving at least one PLGA polymer selected from the group consisting of PLGA 5050 1A, PLGA 8515 3CE, and PLGA 5050 5E in tetrahydrofuran. In certain embodiments, the method comprises contacting the tetrahydrofuran solution with deionized water. In certain embodiments, the method comprises stirring the solution to form a PLGA nanoparticle precipitate. In certain embodiments, the method comprises isolating the PLGA nanoparticle precipitate. In certain embodiments, the method comprises suspending the PLGA nanoparticles in an aqueous suspension. In certain embodiments, the method comprises contacting the aqueous suspension with an aqueous solution comprising the polypeptide. In an exemplary embodiment, the polypeptide is hGH.

In certain embodiments, the aqueous suspension and the aqueous solution both have a pH of about 6.5 to about 7.5. In other embodiments, the aqueous suspension and aqueous solution both have a pH of about 7.2. In certain embodiments, the ionic strength of the aqueous suspension is about 10 mM. In other embodiments, the ionic strength of the aqueous solution is about 10 mM.

Methods

In one aspect, the invention provides a method of treating human growth hormone deficiency in a subject in need thereof. In another aspect, the invention provides a method of delivering a polypeptide to the lungs of a subject. In yet another aspect, the invention provides a method of treating a respiratory disorder in a subject in need thereof.

In certain embodiments, the method comprises administering to the subject a therapeutically effective amount of the composition of the invention.

In certain embodiments, the particles of the composition are capable of degrading in a reasonably short time. In other embodiments, the degradation of particles is required for avoiding excessive accumulation of the particles within the subject. For example, the particles intended for lung deposition must degrade in a reasonably short time to avoid overloading the lungs with the successive doses.

The regimen of administration may affect what constitutes an effective amount. The therapeutic formulations can be administered to the subject either prior to or after the onset of a disease or disorder contemplated in the invention. Further, several divided dosages, as well as staggered dosages can be administered daily or sequentially, or the dose can be continuously infused, or can be a bolus injection. Further, the dosages of the therapeutic formulations can be proportionally increased or decreased as indicated by the exigencies of the therapeutic or prophylactic situation.

Administration of the compositions of the present invention to a patient, preferably a mammal, more preferably a human, can be carried out using known procedures, at dosages and for periods of time effective to treat a disease or disorder contemplated in the invention. An effective amount of the therapeutic compound necessary to achieve a therapeutic effect can vary according to factors such as the state of the disease or disorder in the patient; the age, sex, and weight of the patient; and the ability of the therapeutic compound to treat a disease or disorder contemplated in the invention. Dosage regimens can be adjusted to provide the optimum therapeutic response. For example, several divided doses can be administered daily or the dose can be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions of this invention can be varied so as to obtain an amount of the active ingredient that is effective to achieve the desired therapeutic response for a particular patient, composition, and mode of administration, without being toxic to the patient.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In certain embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease or disorder contemplated in the invention.

In certain embodiments, the compositions of the invention are formulated using one or more pharmaceutically acceptable excipients or carriers. In certain embodiments, the pharmaceutical compositions of the invention comprise a therapeutically effective amount of a compound of the invention and a pharmaceutically acceptable carrier.

The carrier can be a solvent or dispersion medium containing, for example, water, ethanol, polyol (for example, glycerol, propylene glycol, and liquid polyethylene glycol, and the like), suitable mixtures thereof, and vegetable oils.

In certain embodiments, the compositions of the invention are administered to the patient in dosages that range from one to five times per day or more. In other embodiments, the compositions of the invention are administered to the patient in range of dosages that include, but are not limited to, once every day, every two, days, every three days to once a week, and once every two weeks. It is readily apparent to one skilled in the art that the frequency of administration of the various combination compositions of the invention varies from individual to individual depending on many factors including, but not limited to, age, disease or disorder to be treated, gender, overall health, and other factors. Thus, the invention should not be construed to be limited to any particular dosage regime and the precise dosage and composition to be administered to any patient is determined by the attending physical taking all other factors about the patient into account.

Compounds of the invention for administration can be in the range of from about 1 µg to about 10,000 mg, about 20 µg to about 9,500 mg, about 40 µg to about 9,000 mg, about 75 µg to about 8,500 mg, about 150 µg to about 7,500 mg, about 200 µg to about 7,000 mg, about 3050 µg to about 6,000 mg, about 500 µg to about 5,000 mg, about 750 µg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments therebetween.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of a disease or disorder contemplated in the invention.

Formulations can be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations can be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., anti-Alzheimer's Disease agents, anti-tuberculosis agents.

Routes of administration of any of the compositions of the invention include oral, nasal, rectal, intravaginal, parenteral, buccal, sublingual or topical. The compounds for use in the invention can be formulated for administration by any suitable route, such as for oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. The compositions intended for oral use can be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets can be uncoated or they can be coated by known techniques for elegance or to delay the release of the active ingredients. Formulations for oral use may also be presented as hard gelatin capsules wherein the active ingredient is mixed with an inert diluent.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations can be prepared, packaged, or sold in a form suitable for bolus administration or for continuous administration. Injectable formulations can be prepared, packaged, or sold in unit dosage form, such as in ampules or in multidose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In certain embodiments of a formulation for parenteral administration, the active ingredient is provided in dry (i.e., powder or granular) form for reconstitution with a suitable vehicle (e.g., sterile pyrogen-free water) prior to parenteral administration of the reconstituted composition.

Buccal, Pulmonary, Inhalational, Intranasal Administration, and so Forth

A pharmaceutical composition of the invention may be prepared, packaged, or sold in a formulation suitable for pulmonary administration via the buccal cavity. Such a formulation may comprise dry particles that comprise the active ingredient and have a diameter in the range from about 0.5 to about 7 nanometers, and in certain embodiments from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. In certain embodiments, such powders comprise particles wherein at least 98% of the particles by weight have a diameter greater than 0.5 nanometers and at least 95% of the particles by number have a diameter less than 7 nanometers. In certain embodiments, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (in certain embodiments having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration in certain embodiments have an average diameter in the range from about 0.1 to about 200 nanometers.

The pharmaceutical composition of the invention may be delivered using an inhalator such as those recited in U.S. Pat. No. 8,333,192 B2, which is incorporated herein by reference in its entirety.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken, i.e. by rapid inhalation through the nasal passage from a container of the powder held close to the nares. Formulations suitable for nasal administration may, for example, comprise from about as little as 0.1% (w/w) and as much as 100% (w/w) of the active ingredient, and may further comprise one or more of the additional ingredients described herein.

Additional Administration Forms

Additional dosage forms of this invention include dosage forms as described in U.S. Pat. Nos. 6,340,475; 6,488,962; 6,451,808; 5,972,389; 5,582,837; and 5,007,790. Additional dosage forms of this invention also include dosage forms as described in U.S. Patent Applications Nos. 20030147952; 20030104062; 20030104053; 20030044466; 20030039688; and 20020051820. Additional dosage forms of this invention also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Controlled Release Formulations and Drug Delivery Systems

In certain embodiments, the formulations of the present invention can be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time can be as long as a month or more and should be a release which is longer that the same amount of agent administered in bolus form.

For sustained release, the compounds can be formulated with a suitable polymer or hydrophobic material that provides sustained release properties to the compounds. As such, the compounds for use the method of the invention can be administered in the form of microparticles, for example, by injection or in the form of wafers or discs by implantation.

In certain embodiments of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that may, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing

The therapeutically effective amount or dose of a compound of the present invention depends on the age, sex and weight of the patient, the current medical condition of the patient and the progression of a disease or disorder contemplated in the invention. The skilled artisan is able to determine appropriate dosages depending on these and other factors.

A suitable dose of a compound of the present invention can be in the range of from about 0.01 mg to about 5,000 mg per day, such as from about 0.1 mg to about 1,000 mg, for example, from about 1 mg to about 500 mg, such as about 5 mg to about 250 mg per day. The dose can be administered in a single dosage or in multiple dosages, for example from 1 to 4 or more times per day. When multiple dosages are used, the amount of each dosage can be the same or different. For example, a dose of 1 mg per day can be administered as two 0.5 mg doses, with about a 12-hour interval between doses.

It is understood that the amount of compound dosed per day can be administered, in non-limiting examples, every day, every other day, every 2 days, every 3 days, every 4 days, or every 5 days. For example, with every other day administration, a 5 mg per day dose can be initiated on Monday with a first subsequent 5 mg per day dose administered on Wednesday, a second subsequent 5 mg per day dose administered on Friday, and so on.

In the case wherein the patient's status does improve, upon the doctor's discretion the administration of the inhibitor of the invention is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, as a function of the disease or disorder, to a level at which the improved disease is retained. In certain embodiments, patients require intermittent treatment on a long-term basis upon any recurrence of symptoms and/or infection.

The compounds for use in the method of the invention can be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form can be for a single daily dose or one of multiple daily doses (e.g., about 1 to 4 or more times per day). When multiple daily doses are used, the unit dosage form can be the same or different for each dose.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies preferably within a range of circulating concentrations that include the $ED_{50}$ with minimal toxicity. The dosage optionally varies within this range depending upon the dosage form employed and the route of administration utilized.

Definitions

As used herein, each of the following terms has the meaning associated with it in this section.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

Generally, the nomenclature used herein and the laboratory procedures in tissue engineering and biomaterial science are those well-known and commonly employed in the art.

As used herein, the articles "a" and "an" refer to one or to more than one (i.e., to at least one) of the grammatical object of the article. By way of example, "an element" means one element or more than one element.

As used herein, the term "about" is understood by persons of ordinary skill in the art and varies to some extent on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, nasal, pulmonary and topical administration.

A "disease" as used herein is a state of health of an animal wherein the animal cannot maintain homeostasis, and wherein if the disease is not ameliorated then the animal's health continues to deteriorate.

A "disorder" as used herein in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the term "microsphere" refers to a spherical or spheroid particle with a diameter in the range of about 1 µm to about 1 mm. In certain embodiments, microspheres comprise one or more layers, optionally including an outer shell layer, while in other embodiments, microspheres do not comprise layers or an outer shell.

As used herein, the term "monodisperse" refers to a particle based composition comprising particles that are substantially uniform in size, shape and mass. In certain embodiments, a monodisperse composition of microspheres contains particles of nearly the same size, forming a narrow distribution about an average value, whereas a polydisperse suspension contains particles of different sizes, forming a broad distribution.

In certain embodiments, monodisperse or near-monodisperse particles have equal to or less than about 15% coefficient of variation. In other embodiments, monodisperse particles have equal to or less than about 5% coefficient of variation (that is, $CV=\sigma/d<5\%$, where $\sigma$ and $d$ are the standard deviation and the mean size, respectively). In yet other embodiments, the monodisperse particles have equal to or less than about 5%, 2%, or 1%.

The term "monomer" refers to any discreet chemical compound of any molecular weight.

As used herein, the term "nanosphere" refers to a spherical or spheroid particle with a diameter in the range of about 1 nm to about 100 nm.

The terms "patient," "subject" or "individual" are used interchangeably herein, and refer to any animal, or cells thereof whether in vitro or in situ, amenable to the methods described herein. In a non-limiting embodiment, the patient, subject or individual is a human.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that can be included in the pharmaceutical compositions used in the practice of the invention are known in the art and described, for example in Remington's Pharmaceutical Sciences (Genaro, Ed., Mack Publishing Co., 1985, Easton, PA), which is incorporated herein by reference.

As used herein, the language "pharmaceutically acceptable salt" refers to a salt of the administered compounds prepared from pharmaceutically acceptable non-toxic acids, including inorganic acids, organic acids, solvates, hydrates, or clathrates thereof.

As used herein, the term "polymer" refers to a molecule composed of repeating structural units typically connected by covalent chemical bonds. The term "polymer" is also meant to include the terms copolymer and oligomers. In certain embodiments, a polymer comprises a backbone (i.e., the chemical connectivity that defines the central chain of the polymer, including chemical linkages among the various polymerized monomeric units) and a side chain (i.e., the chemical connectivity that extends away from the backbone).

The term "prevent," "preventing" or "prevention," as used herein, means avoiding or delaying the onset of symptoms associated with a disease or condition in a subject that has not developed such symptoms at the time the administering of an agent or compound commences.

A "therapeutic" treatment is a treatment administered to a subject who exhibits signs of pathology, for the purpose of diminishing or eliminating those signs.

As used herein, the term "therapeutically effective amount" refers to an amount that is sufficient or effective to prevent or treat (delay or prevent the onset of, prevent the progression of, inhibit, decrease or reverse) a disease or condition described or contemplated herein, including alleviating symptoms of such disease or condition.

As used herein, the term "treatment" or "treating" is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has a condition contemplated herein, a symptom of a condition contemplated herein or the potential to develop a condition contemplated herein, with the purpose to cure, heal, alleviate, relieve, alter, remedy, ameliorate, improve or affect a condition contemplated herein, the symptoms of a condition contemplated herein or the potential to develop a condition contemplated herein. Such treatments may be specifically tailored or modified, based on knowledge obtained from the field of pharmacogenomics.

Throughout this disclosure, various aspects of the invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The following abbreviations are used herein: BSA, Bovine serum albumin; CD, Circular dichroism; Dh, Hydrodynamic diameter; DLS, Dynamic light scattering; $g/cm^3$, Gram per cubic centimeter; hGH, Human growth hormone; kDa, Kilodalton; MES, 2-(N-morpholine)-ethane sulphonic acid; min, Minute; mg, Milligram; ml, Milliliter; MW, Molecular weight; MWCO, Molecular weight cut off; nm, Nanometer; PDI, Polydispersity index; pI, Isoelectric point; PLGA 5050 1A, Poly (lactic-co-glycolic) acid uncapped polymer, ~10 kDa; PLGA 8515 3CE, Poly (lactic-co-glycolic) acid ester endcapped polymer, ~30 kDa; PLGA 5050 5E, Poly (lactic-co-glycolic) acid ester endcapped polymer, ~50 kDa; r-hGH, Recombinant human growth hormone; SD, Standard Deviation; Trp, Tryptophan; Tyr, Tyrosine; UV, Ultraviolet; V, Volume; r, Surface Coverage; rPL, Plateau Surface Coverage; % w/v, Percentage weight by volume; PS, Polystyrene.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials

Recombinant human growth hormone (r-hGH) was obtained from Bresagen, Inc. (Adelaide, Australia) in the form of a lyophilized powder and was used without further purification. PLGA nanoparticles were prepared using PLGA 50501A, PLGA 5050E and PLGA 8515 E which were obtained from Evonik Corporation (Parsippany, NJ). Nanopure water used to make buffer solutions and to reconstitute lyophilized protein was purified by reverse osmosis (Barnstead Ultrafiltered type I water). All buffer components (acetic acid, MES, sodium chloride, sodium hydroxide and hydrochloric acid) were of analytical grade and purchased from Sigma-Aldrich (St. Louis, MO). Other experimental materials were acquired from Fisher Scientific Co. (Fairlawn, NJ).

Preparation of Buffer Solutions

Buffer solutions were prepared in nanopure water at 10 mM ionic strength for each pH condition: pH 4.0 (acetate), isoelectric pH 5.3 (MES), and neutral pH 7.2 (MES). The pH of each buffer solution was adjusted to the desired value using 1 N sodium hydroxide or 1 N hydrochloric acid and the ionic strength was adjusted to 10 mM using sodium chloride.

Preparation of PLGA Nanoparticles

PLGA nanoparticles were prepared by nanoprecipitation based on the diffusion of the organic solvent from a polymer solution into an aqueous phase leading to the precipitation of the polymer into small colloidal particles. PLGA was dissolved in tetrahydrofuran at a concentration of 1 mg/ml to 10 mg/ml. 1 ml of the organic solution was quickly injected in to 10 mL Nanopure water under magnetic stirring. The dispersion was kept under stirring conditions to allow solvent evaporation and hardening of nanoparticles for 3-4 hours. The nanoparticles were prepared using PLGA of different molecular weight and lactic to glycolic acid ratio to achieve different degree of hydrophobicity of the particles. PLGA 5050 1A (10 kDa), PLGA 8515 3CE (30 kDa) and PLGA 5050 5E (50 kDa) were used in preparation of nanoparticles.

The nanoparticles dispersed in water and different buffer media were characterized for size, polydispersity index (pdi) and zeta potential by Dynamic Light Scattering (DLS) using Malvern Instrument's Zetasizer, Nano ZS (ZEN3600, measurement range of 0.6 nm to 6 µm). Dilute dispersion of nanoparticles was prepared by adding nanoparticles to the 1 ml Eppendorf centrifuge tube containing purified water or buffer dialysate, gently stirred for ~2 seconds on a vortex stirrer (Vortexgenie, K-550-G, Scientific-Industries, Inc.) and then transferred to the disposable low volume cuvettes (ZEN0112) designed by Malvern Instruments for size analysis using calibrated micropipette (Eppendorf Research pro). Zeta potential measurements of the same sample were done separately in a folded capillary cell (DTS1060) designed especially for zeta potential measurements.

Preparation of Protein Solution and PLGA Nanoparticle Suspension

The concentrations of protein and polymer were chosen to remain within the scattering limits allowed for spectroscopic study. Protein stock solution was prepared by reconstituting lyophilized r-hGH with pre-filtered nanopure water. Dialysis of protein solution and PLGA nanoparticle suspension (each in separate dialysis bag) was carried out against appropriate buffer, 400 times the volume of the sample for ~2-4 hours using 3500 MWCO regenerated cellulose membrane for system equilibration. After dialysis, the protein solution was filtered using 0.22 μm syringe filter to remove any aggregated species and using the known specific absorptivity of r-hGH at 277 nm ($A_{277\ nm}$=0.93 at 1 cm, 0.100%), the protein concentration was determined in a Shimadzu UV-1601 Spectrophotometer.

PLGA 5050 1A nanoparticles were prepared at 1.63 mg/ml while 8515E and 5050E nanoparticles were prepared at a concentration of 0.122 mg/ml for all three studies—DLS, fluorescence spectroscopy and CD.

Protein concentrations were adjusted in the range of 0.001 to 0.2 mg/ml (i.e. 0.056 μM to 9.09 μM) for DLS study. Working concentration of protein in the range of 0.014 to 0.15 mg/ml (i.e. 0.63 μM to 6.82 μM) was used for fluorescence spectroscopy studies to obtain protein covered PLGA nanoparticles at low and complete surface coverage. Circular dichroism studies were conducted using protein concentration in the range of 0.065-0.15 mg/ml (i.e. 2.95 μM to 6.82 μM) at low and complete surface coverage of the nanoparticles. The protein concentrations were adjusted using the dialysate for each of the studies.

Surface coverage of r-hGH on nanoparticles was experimentally determined using equilibrium micro-dialysis in 96 well plate followed by fluorescence spectroscopy. 100 μl of Nanoparticle suspension and 100 μl r-hGH solution of known concentration separated by a 100 kDa semipermeable regenerated cellulose membrane were allowed to equilibrate at room temperature for 3-4 hours. Concentration of free r-hGH was measured using fluorescence spectroscopy with excitation wavelength set at 295 nm and measuring fluorescence emission intensity at 327 nm. The amount of r-hGH adsorbed onto polymer surface was then calculated by using the below mentioned equation.

$$C_b = C_0 - 2C_f \quad (1)$$

where $C_b$ is the bound protein concentration, $C_0$ is the initial protein concentration and $2C_f$ is the total free protein concentration Dynamic Light Scattering (DLS)

Increasing amounts of r-hGH solution were added to the cuvettes containing PLGA nanoparticles suspension in a buffer medium to attain concentration in the range of 0.001 to 0.2 mg/ml just before size measurement. The change in particle size as a result of protein adsorption was determined by DLS using Malvern Instrument's Zetasizer Nano ZS (ZEN3600) at time zero and at 30 minute time intervals. DLS measures the time-dependent fluctuations in the intensity of the scattered light depending on the Brownian motion of particles, which then relates it to the hydrodynamic diameter of the particles using Stokes-Einstein equation.

Fluorescence Spectroscopy

Fluorescence spectra were measured with a Tecan i3 fluorescence spectrophotometer using 96 well black quartz plate. The temperature of the sample was maintained at 25° C. in all experiments. In the manual mixing adsorption experiments, the nanoparticles were added to the stirred protein solution with an automatic pipette. Excitation wavelength was set at 295 nm (for r-hGH), with excitation and emission slits at 5 nm. Fluorescence emission data was collected from 305 to 400 nm for the r-hGH in solution and adsorbed on nanoparticles. A blank, containing all components except protein, was subtracted from each sample. The % quenching was obtained from the peak height.

Circular Dichroism Spectroscopy

Solutions of r-hGH as well as suspensions of r-hGH adsorbed onto PLGA nanoparticles and their corresponding reference samples (buffer solutions or suspensions of PLGA in buffers) were scanned over a wavelength range of 320 nm-250 nm for tertiary structure and 240 nm-200 nm for secondary structure determination in an Aviv CD spectrometer. The r-hGH concentration range for near UV scans was 0.3-0.6 mg/mL, while that for far-UV scans was 0.065-0.15 mg/mL. The cell path length was 0.5 cm for near UV scans (320 nm-250 nm) and 0.1 cm for far UV scans (250 nm-200 nm) with a bandwidth of 1.0 nm for both UV ranges. Appropriate reference scans were subtracted from the sample scan to obtain the net CD scans for r-hGH, and the data were converted to mean residue weight ellipticity ($^{MRW}\theta$) using a mean residue weight (MRW) of 115 for r-hGH. In order to compare with previously published values, the α-helical contents of r-hGH solutions were initially estimated from the absolute ellipticity values obtained at 209 nm and 222 nm using the following equations:

$$\%\ \alpha\ \text{helix from}\ [\Theta]_{222} = \frac{[\theta]222 + 4800}{45400} \times 100 \quad (2)$$

$$\%\ \alpha\ \text{helix from}\ [\Theta]_{209} = \frac{[\theta]209 - 2200}{36200} \times 100 \quad (3)$$

The secondary spectral data of r-hGH solution and that bound to PLGA particles was also analyzed using CDSSTR and CONTIN software (CDPro Suite). Based on preliminary analysis, a reference data set comprising secondary spectral data in a wide wavelength range (180-240 nm) on 43 soluble and 6 denatured proteins gave the best overall fit for r-hGH in solution as well as for adsorbed r-hGH samples and was chosen for use in the analyses.

Isothermal Titration Calorimetry (ITC)

calorimetric study for the binding of r-hGH onto different grades of PLGA nanoparticles was performed using an Affinity ITC, TA instruments microcalorimeter. All experiments were performed at 25° C. In addition, experiments were performed at 15° C. for PLGA 5050 1A na-noparticles to study ΔCp. Protein solution and nanoparticles suspension were dialyzed, as discussed elsewhere herein, the dialyzate was used for reference runs. Both, r-hGH solutions and PLGA suspensions were degassed under vacuum prior to use. The r-hGH solution was placed in 96 well auto sampler plate for syringe while PLGA nanoparticle suspension and reference buffer dialysate were placed in 96 well auto sampler plate for cell. Before the beginning of each titration, the sample cell, syringe and auto sampler assembly were thoroughly washed with proper detergent solution and deionized water as a part of cleaning cycle. The experiments consisted of a series of injections of r-hGH (ligand) solutions from a 250 µl syringe into PLGA nanoparticles suspension (macromolecule) in the cell (V=170 µl). For each binding isotherm, 11-15 automatic injections were made, the injection duration being ~14 s. The volumes of r-hGH solution delivered were identical (10 µl) for each injection within a set and were spaced at 300 seconds interval to allow complete equilibration between injections. The stirring speed was set at 75 rpm to ensure rapid mixing but to not cause foaming of the protein solution. The differential heating power needed to maintain zero temperature difference between the reference and the sample cell after injection of the titrant was recorded versus time. Each such binding titration was performed in triplicate under the influence of different pH and ionic strength of the solution. Heats of dilution were determined in separate control experiments by injecting protein solution into the dialyzate (reference run) and were subtracted from the heats determined in corresponding protein-PLGA binding experiments, and then normalized to protein and PLGA concentration.

The result of chemical reaction occurring upon each injection of r-hGH into nanoparticle suspension is either release or absorption of heat (qi) proportional to the amount of protein that binds to the nanoparticle surface in a particular injection (v×Δpi) and the characteristic binding enthalpy (ΔH) for the reaction (Leavitt S. et. al., *Curr. Opin. Struct. Biol.* 11 (5), 560-566 (2001))

$$qi = v \times \Delta H \times \Delta Pi$$

where v is the volume of the reaction cell and ΔPi is the increase in the concentration of bound protein after the ith injection. The ITC instrument works by power compensation to maintain the temperature of the sample cell. Thus, the instrumental response (measured signal) is the amount of power (microcalories per second) necessary to maintain the constant temperature difference between the reaction and reference cells and the heat after each injection is therefore obtained by calculating the area under each peak (Leavitt S. et. al., *Curr. Opin. Struct. Biol.* 11 (5) 560-566(2001 October)). The binding curve is then obtained from a plot of the heats from each injection against the ratio of protein and nanoparticles in the cell. The binding curve is analyzed with the appropriate binding model to determine Ka (binding affinity), n (number of binding sites) and ΔH (enthalpy). ΔG is then calculated using an equation:

$$\Delta_{ads} G = -RT \ln Ka$$

where R is the gas constant in cal/molK and T is the absolute temperature in K.

The entropy change of the interaction is obtained by using the standard thermodynamic expression:

$$\Delta_{ads} G = \Delta_{ads} H - T\Delta_{ads} S$$

The heat capacity $\Delta_{ads}C_p$ associated with the binding reaction can be obtained by performing the experiments at two different temperatures and it is calculated using an equation:

$$\Delta_{ads}C_p = \frac{\Delta adsH2 - \Delta adsH1}{T2 - T1}$$

$\Delta_{ads}C_p$ reflects conformational and configurational changes that occur during the adsorption process (Brandts F. et. al, *Marcel Dekker publication*, New York, p. 213. (1969); Parikh, V. et. al. *AAPS PharmSciTech*, 19(7), 3040-304 (2018)). The ITC results from the binding isotherms were fitted for a model of a single set of identical sites by means of non-linear least squares fitting using Nanoanalyze software from TA instrument that yielded fit parameters: Ka (equilibrium binding constant), ΔH (association enthalpy change) and n (stoichiometry of the association). Number of proteins per µm² of nanoparticle surface area was calculated from n, stoichiometry of binding. Attempts were made to fit the binding data to models for two binding sites but in no instance was a better fit obtained i.e. the fits of two binding sites model were reasonably similar to that of one-site model. Concentrations of titrant (r-hGH) and the sample in the cell (PLGA) were calculated automatically by the instrument software.

Example 1: Synthesis of PLGA Nanoparticles Loaded with r-hGH

PLGA nanoparticles smaller than 100 nm were obtained with all three grades of PLGA. Zeta potential of acid uncapped PLGA 5050 1A nanoparticles was −65.6±3.8, −54.2±3.5 and −36.8±4.2 at pH 7.2, 5.3 and 4.0 respectively, zeta potential of ester end capped PLGA 8515 3CE nanoparticles was −51.4±4.6 and −26.4±3.7 at pH 7.2 and 5.3 respectively whereas zeta potential of ester end capped PLGA 5050 5E nanoparticles was −45.3±4.1 and −25.5±5.9 at pH 7.2 and 5.3 respectively. For ester end capped polymer nanoparticles, the zeta potential evaluation at pH 4.0 was not possible due to aggregation of particles at this pH condition. The results for size and zeta potential of PLGA nanoparticles are described in Table I.

Surface coverage of r-hGH with respect to mg/m² of PLGA nanoparticles and ratio of r-hGH to PLGA nanoparticles is described in Table II. The adsorption of r-hGH onto PLGA 50501A was found to be high at the pH of 5.3 (0.3 mg/m²) followed by pH 4.0 (0.23 mg/m²) followed by pH 7.2 (0.19 mg/m²). The same trend was observed for PLGA 8515 3CE with higher adsorption at pH 5.3 (3.83 mg/m²) followed by pH 7.2 (3.37 mg/m²) and PLGA 5050 5E nanoparticles with higher adsorption at pH 5.3 (6.37 mg/m²) followed by pH 7.2 (5.13 mg/m²). The ratio of r-hGH to PLGA nanoparticles was found to be 1:0.21 and 1:0.17 at pH 7.2 and pH 5.3 respectively with PLGA 5050 5E; 1:3.86 and 1:3.39 at pH 7.2 and 5.3 respectively with PLGA 8515 3CE and 1:5.79, 1:3.67 and 1:4.78 at pH 7.2, 5.3 and 4.0 respectively with PLGA 50501A whereas this ratio in Nutropin depot was 1:5.1.

pKa of the carboxyl groups of PLGA is about 3.8, therefore, surface charge was expected to be negative for the nanoparticles prepared from PLGA 50501A under all pH conditions studied due to ionization of surface carboxylic groups. However, negative zeta potential was obtained for nanoparticles prepared from all three grades of PLGA under all pH conditions studied. The magnitude of negative zeta potential was in order of pH 7.2>pH 5.3>pH 4.0 while that at any given pH condition was higher for uncapped PLGA 50501A nanoparticles than ester end capped PLGA 8515 3CE and PLGA 5050 5E nanoparticles. This also demonstrated hydrophobicity of nanoparticles in that order based on molecular weight and surface charge on nanoparticles.

At pH 7.2 and 5.3, r-hGH surface coverage onto PLGA nanoparticles follows the trend of PLGA 5050 5E nanoparticles>PLGA 8515 3CE nanoparticle>PLGA 5050 1A nanoparticles and order of hydrophobicity of the polymer surface corroborates this order. Under certain conditions, the ratio of r-hGH to PLGA is higher for these three grades of PLGA compared to Nutropin depot, making these compositions promising for therapeutic hGH delivery purposes.

pH, charge status of r-hGH, magnitude of charge on nanoparticles and hydrophobicity of the polymer grade. The results showed that binding of r-hGH onto PLGA nanoparticles showed a dependency on the solution pH and hydrophobicity of the polymer. The hydrodynamic diameter of r-hGH was about 5 nm which demonstrates the possibility of adsorption of r-hGH in a monolayer on PLGA 5050 1A nanoparticles and multilayer adsorption on PLGA 8515 3CE and PLGA 5050 5E nanoparticles at pH 7.2. At this pH, electrostatic repulsion is expected between the protein and

TABLE I

Physical Characterization of Nanoparticles and r-hGH

| Polymer Type/ r-hGH | Zeta Average ± SD (nm) | PDI | Zeta Potential (mv) ± SD | | |
|---|---|---|---|---|---|
| | | | pH 7.2 | pH 5.3 | pH 4.0 |
| PLGA 50:50 1A | 50 ± 2.3 | 0.084 | −65.6 ± 3.8 | −54.2 ± 3.5 | −36.8 ± 4.2 |
| PLGA 50:50 5E | 49.5 ± 1.8 | 0.093 | −45.3 ± 4.1 | −25.5 ± 5.9 | NA |
| PLGA 85:15 3CE | 60.5 ± 1.6 | 0.075 | −51.4 ± 4.6 | −26.4 ± 3.7 | NA |
| r-hGH | 4 ± 0.9 | 0.085 | −11 ± 3 | 0.985 ± 1 | +15 ± 4 |

TABLE II

Surface coverage r-hGH on to PLGA nanoparticles

| | PLGA 5050 1A Nanoparticles | | PLGA 8515 3CE Nanoparticles | | PLGA 5050 5E Nanoparticles | |
|---|---|---|---|---|---|---|
| pH | Ratio of r-hGH:PLGA NP | mg/m² | Ratio of r-hGH:PLGA NP | mg/m² | Ratio of r-hGH:PLGA NP | mg/m² |
| 7.2 | 1:5.79 | 0.19 | 1:3.86 | 3.37 | 1:0.21 | 5.13 |
| 5.3 | 1:3.67 | 0.3 | 1:3.39 | 3.83 | 1:0.17 | 6.37 |
| 4.0 | 1:4.78 | 0.23 | | | | |

Example 2: Dynamic Light Scattering Studies

Figure 1B:
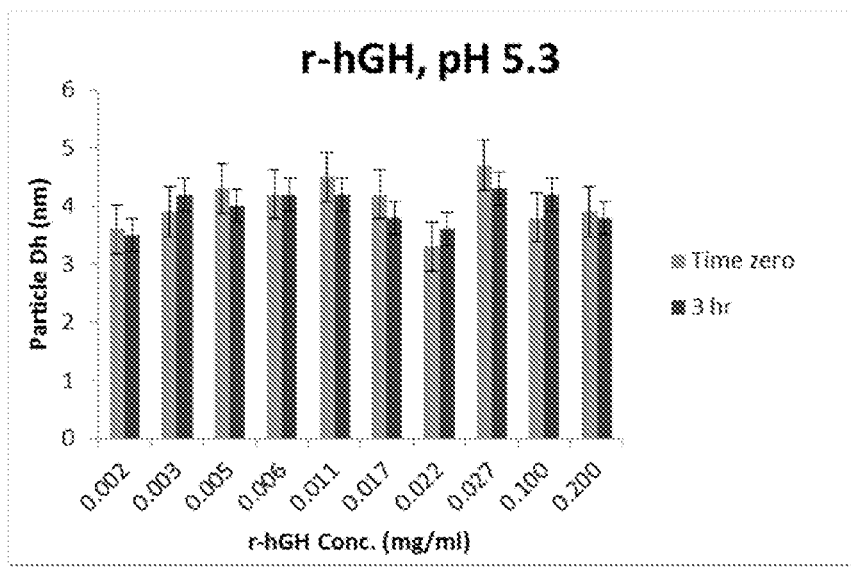
Figure 1C:
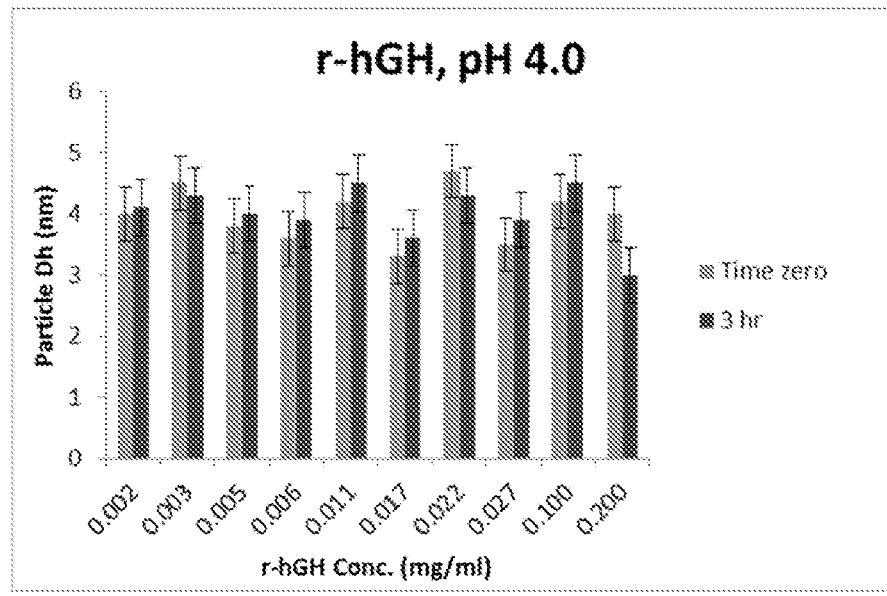
Figure 2A:
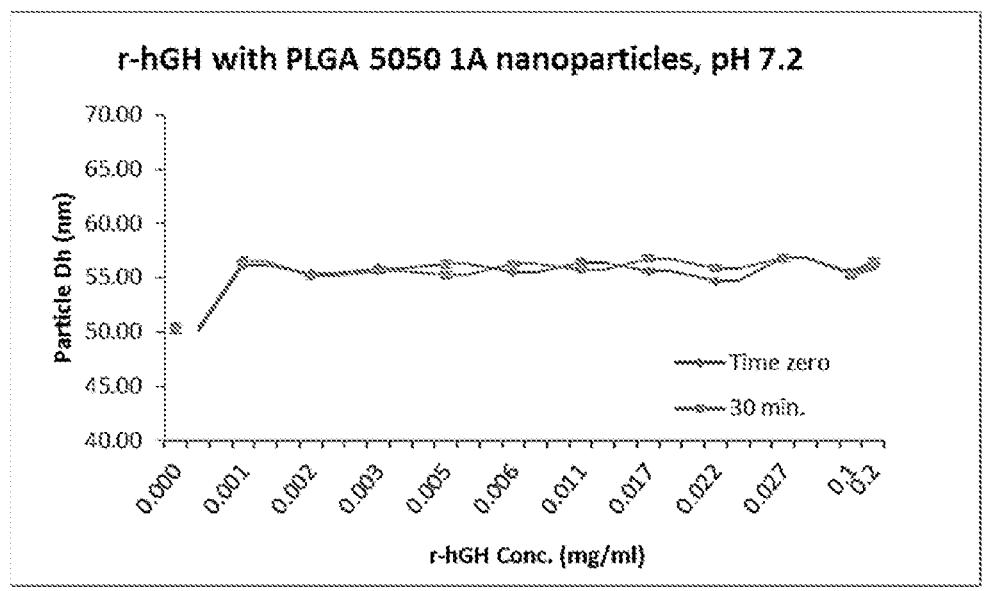
FIGS. 2A-2C are a set of graphs illustrating measurements at pH 7.2 (FIG. 2A), pH 5.3 (FIG. 2B), and pH 4.0 (FIG. 2C), using dynamic light scattering, of hydrodynamic diameter, Dh (nm) of negatively charged PLGA 5050 1A nanoparticle as a function of concentration of r-hGH (mg/ml) at 10 mM ionic strength of the solution. Dh values were measured immediately upon addition of PLGA suspension into the protein-buffer mixture and at 30 minutes into adsorption of the same sample, n=3, SD.
Figure 2B:
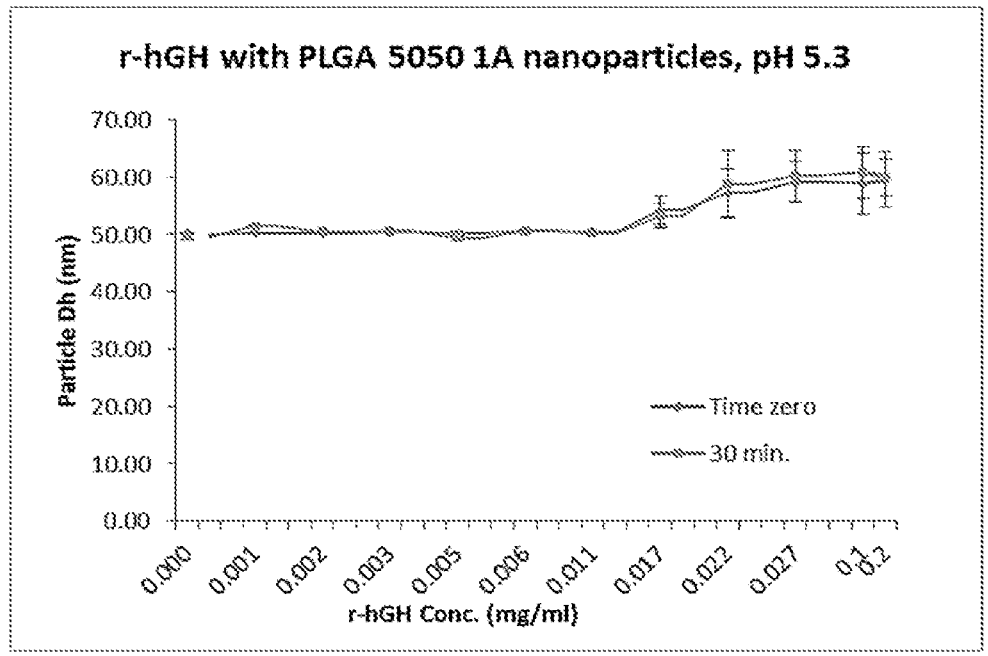
Figure 2C:
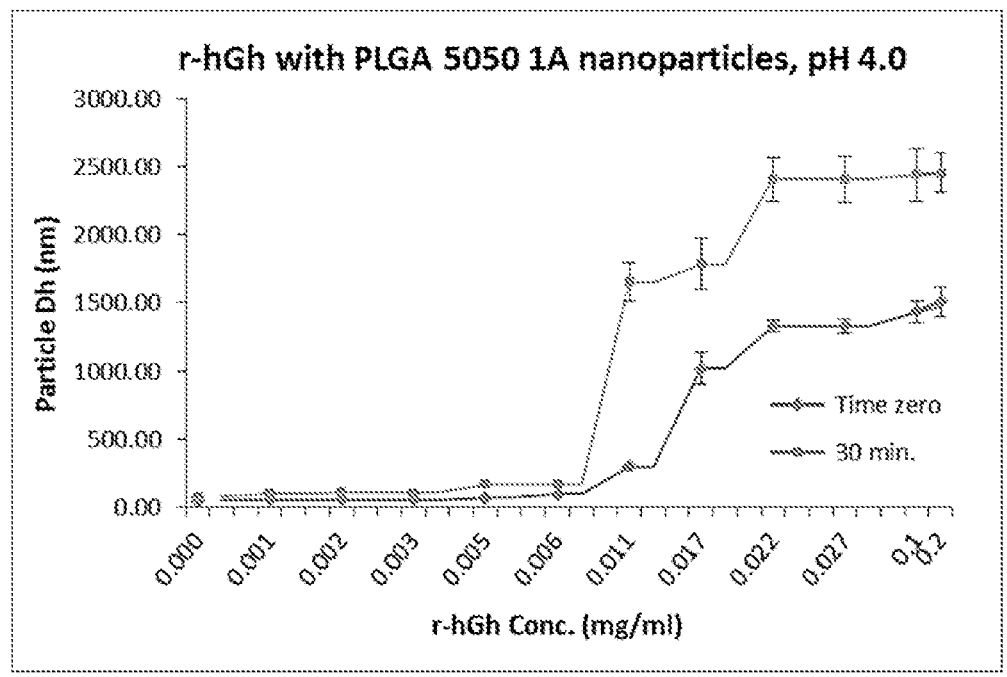
Figure 3A:
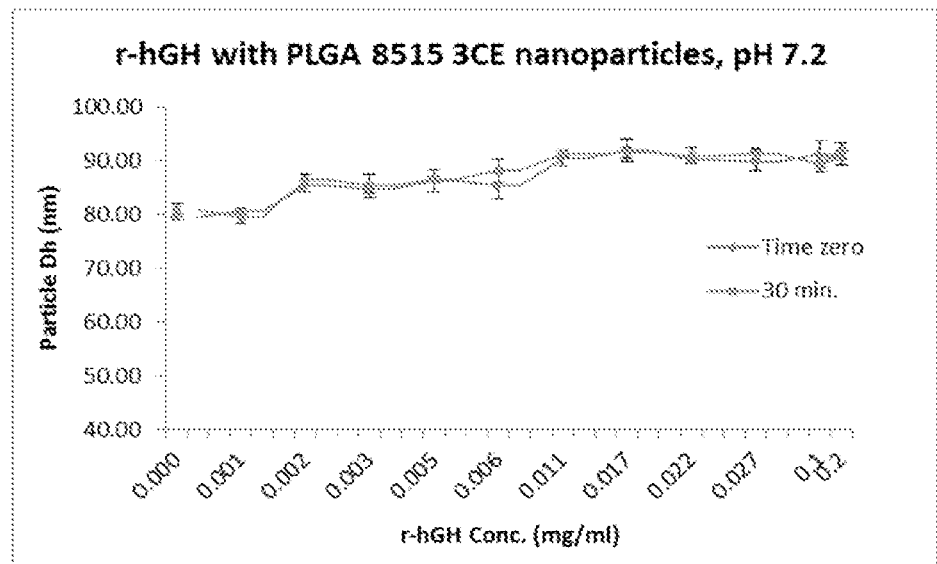
FIGS. 3A-3B are a set of graphs illustrating measurements at pH 7.2 (FIG. 3A) and pH 5.3 (FIG. 3B), using dynamic light scattering, of hydrodynamic diameter, Dh (nm) of negatively charged PLGA 8515 3CE nanoparticle as a function of concentration of r-hGH (mg/ml) at 10 mM ionic strength of the solution. Dh values were measured immediately upon addition of polystyrene suspension into the protein-buffer mixture and at 30 minutes into adsorption of the same sample, n=3, SD.
Figure 3B:
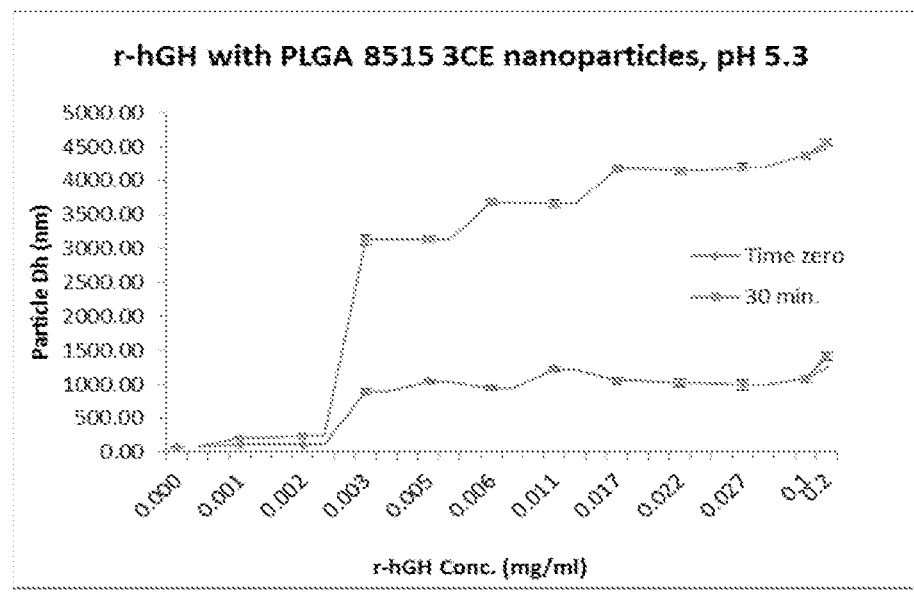
Figure 4A:
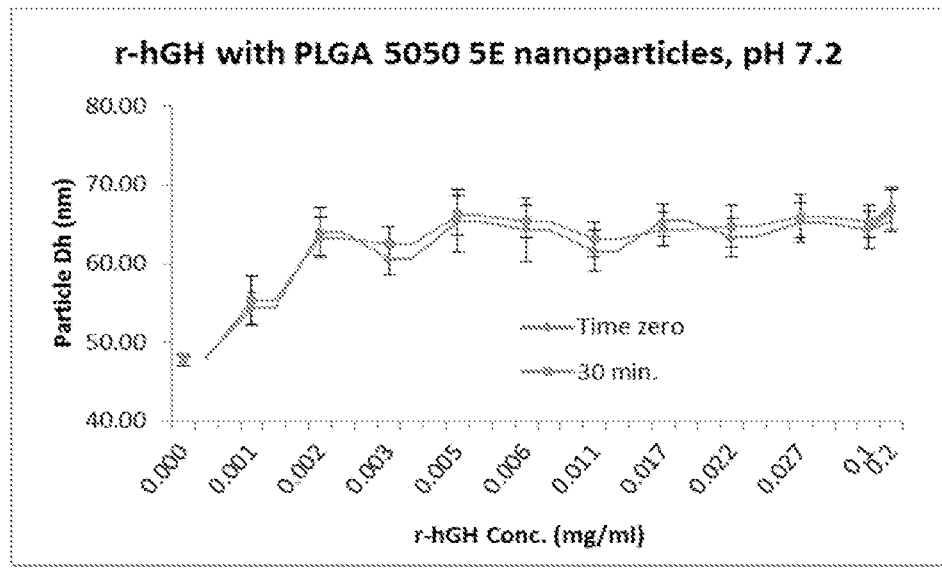
FIGS. 4A-4B are a set of graphs illustrating measurements at pH 7.2 (FIG. 4A) and pH 5.3 (FIG. 4B), using dynamic light scattering, of hydrodynamic diameter, Dh (nm) of negatively charged PLGA 5050 5E nanoparticle as a function of concentration of r-hGH (mg/ml) at 10 mM ionic strength of the solution. Dh values were measured immediately upon addition of PLGA suspension into the protein-buffer mixture and at 30 minutes into adsorption of the same sample, n=3, SD.
Figure 4B:
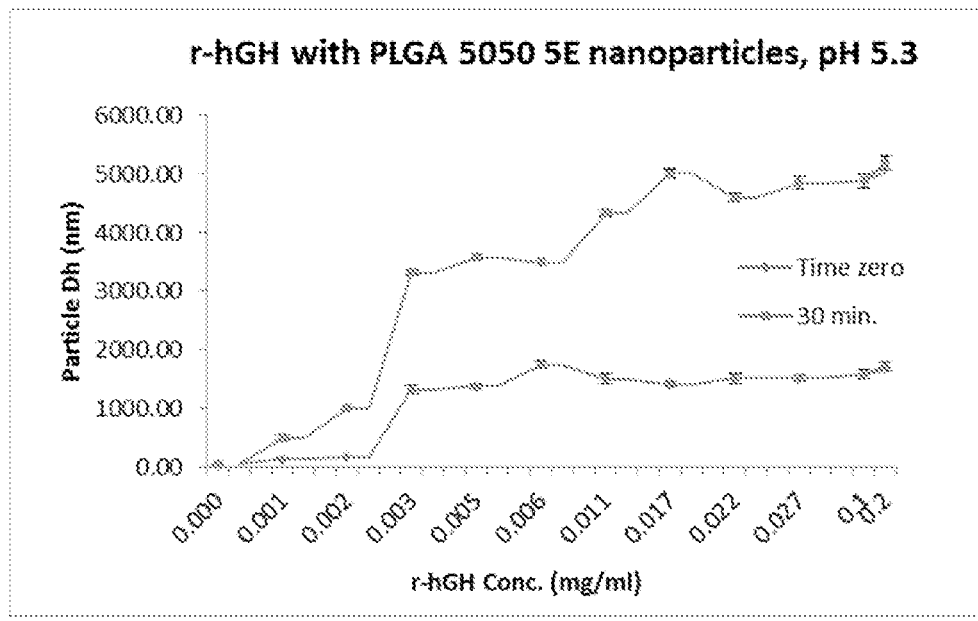

Size analysis of r-hGH in solution as a function of pH at time zero and at 3 hour intervals in different pH condition shows the stability of r-hGH in different buffer media as demonstrated in FIG. 1. The size analyses of r-hGH adsorbed onto PLGA 50501A, PLGA 8515 3CE and PLGA 5050 5E are presented in FIGS. 2A-2C, 3A-3B, and 4A-4B respectively. The change in hydrodynamic diameter ($D_h$) of PLGA nanoparticles (nm) was plotted against the concentration of r-hGH in the mixture (mg/ml). Results from size analysis in FIGS. 2A-2C, 3A-3B, and 4A-4B show that the size of PLGA nanoparticles increases with increasing binding of protein to the surface. At pH 7.2, this increase is on the order of ~6 nm at time zero and 30 minutes for PLGA 5050 1A nanoparticles (FIG. 2A), ~11 nm at time zero and 30 minutes for PLGA 8515 3CE nanoparticles (FIG. 3A) and ~18 nm at time zero and 30 minutes for PLGA 5050 5E nanoparticles (FIG. 4A) At pH 5.3, the increase in size is in the order of ~10 nm at time zero and 30 minutes for PLGA 5050 1A nanoparticles (FIG. 2B), ~1 µm at time zero and ~4 µm at 30 min for PLGA 8515 3CE nanoparticles (FIG. 3B) and ~1.5 µm at time zero and ~5 µm at 30 min for PLGA 5050 5E nanoparticles (FIG. 4B). At pH 4.0, the increase in size is in the order of ~1 µm at time zero and ~3 µm at 30 minutes for PLGA 5050 1A nanoparticles (FIG. 2C), whereas the particles of 8515 E and 5050E were unstable in the buffer at this pH.

The study was conducted to evaluate the change in size of nanoparticles upon interaction with protein as function of PLGA particles. Without intending to be limited to any particular theory, adsorption is therefore likely due to hydrophobic interaction under these conditions. The higher coverage for ester end capped polymer surface compared to uncapped polymer surface can be attributed to the higher hydrophobicity of the surface of nanoparticles prepared from ester end capped PLGA 8515 3CE and 5050 5E in comparison to PLGA 50501A nanoparticles.

The size increase at pH 5.3 for ester end capped PLGA 8515 3CE and 5050 5E nanoparticles and at pH 4.0 for uncapped PLGA 50501A nanoparticles approached several microns both immediately after mixing as well as 30 minutes after mixing. The hydrodynamic diameter of r-hGH is about 5 nm while that of PLGA nanoparticles is about 50-80 nm. Without wishing to be limited to any particular theory, it is therefore unlikely that adsorption was solely a consequence of r-hGH adsorption. The results suggest the occurrence of particle aggregation upon protein adsorption. The process of adsorption at pH 4.0 appears to expose the hydrophobic areas of the protein to the solution, resulting in higher tendency to aggregate. r-hGH is known to be unstable at pH 4.0 owing to increased net charge. Thus, it is reasonable to speculate that the structural rearrangement in r-hGH causes exposure of some of its hydrophobic residues at the already hydrophobic PLGA surface attracting other such surface. This results in particle aggregation causing a very high increase in the particle hydrodynamic diameter. The fact that the particle size continues to increase 30 minutes into adsorption suggests increased agglomeration of the particle as a result of adsorption. At the isoelectric point (pH 5.3), r-hGH is the most stable due to the distribution of relatively equal number of positive and negative charges on the molecule, which results in intramolecular electrostatic attraction favoring a compact structure. The higher strucintensity associated with adsorption of r-hGH onto negatively charged PLGA nanoparticles. It is observed that higher the interaction with nanoparticles (electrostatic or hydrophobic), higher the quenching in fluorescence intensity without major change in $\lambda$max depending on the pH and hydrophobicity of the polymer.

TABLE III

Summary of r-hGH fluorescence adsorbed onto PLGA nanoparticles as a function of solution pH in 10 mM ionic strength of the solution

| PH | Surface coverage | PLGA 5050 1A nanoparticles | | PLGA 8515 3CE nanoparticles | | PLGA 5050 5E nanoparticles | |
|---|---|---|---|---|---|---|---|
| | | shift in $\lambda$max (nm) | % reduction in intensity | Blue shift in $\lambda$max (nm) | % reduction in intensity | shift in $\lambda$max (nm) | % reduction in intensity |
| 7.2 | 0.3 rPL | NA | 28 | NA | 36 | 6 (blue Shift) | 49 |
| | rPL | NA | 39 | NA | 37 | NA | 30 |
| 5.3 | 0.3 rPL | NA | 26 | NA | 36 | NA | 45 |
| | rPL | NA | 35 | NA | 38 | NA | 47 |
| 4.0 | 0.3 rPL | 5 (red shift) | 68 | | | | |
| | rPL | 1 (red shift) | 66 | | | | | tural stability due to lack of net charge and hence, minimal electrostatic repulsion between adsorbed protein molecules may have led to a closer packing on the surface than at the pH where r-hGH carries a net charge. However, when the exposed hydrophobic parts come in contact with water specially at higher concentrations, they may become energetically unstable since the native structure of globular protein in aqueous solution is only marginally stable. Moreover, prior to adsorption, a partial dehydration of the structured water layer around the PLGA 8515 3CE and PLGA 5050 5E surface and the r-hGH surface may have caused water molecules to gain freedom. Since hydrophobic surfaces have a low affinity for water molecules, the r-hGH may have changed its conformation to remove contact of these regions with the aqueous environment by either burying the hydrophobic region internally or associating with similar regions on the PLGA surface. The arrangement of r-hGH at PLGA 8515 3CE and 5050 5E surface may have been such that it resulted in exposure of hydrophobic residues causing particle aggregation. However, at pH 5.3 for 5050 1A particle, a size increase of only 10 nm indicates adsorption of nanoparticles without particle aggregation. Without wishing to be limited by any theory, this can be attributed to less hydrophobic interaction and lesser structural arrangements depending on low hydrophobicity of this polymer grade.

Example 3: Fluorescence Spectroscopy

Figure 5:
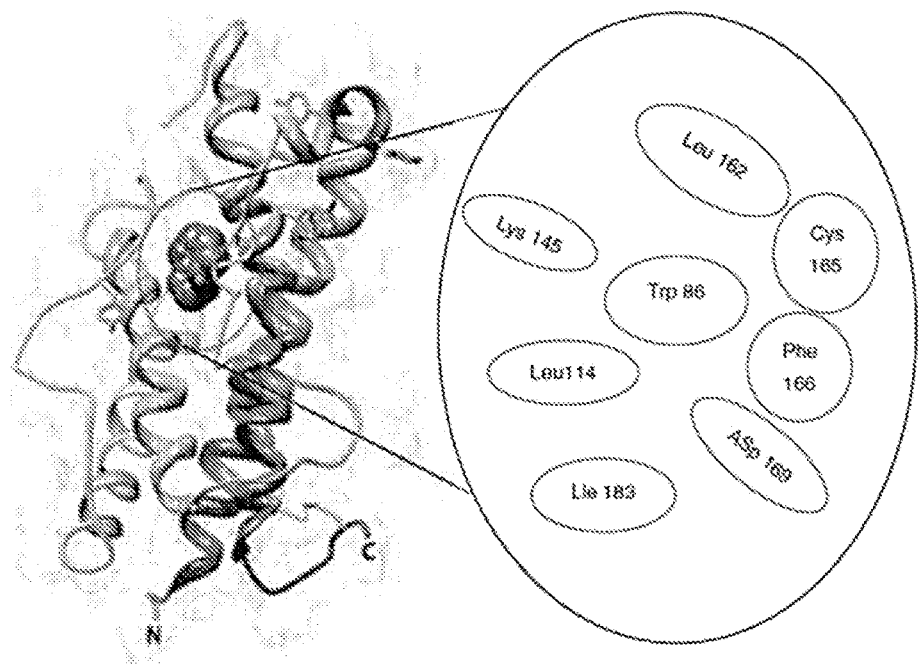
FIG. 5 illustrates the three-dimensional structure of r-hGH. Tryptophan 86 is space filling and the eight residues are sticks. The right hand side indicates the amino acid residues that create the moderately hydrophobic environment of tryptophan 86.
Figure 6A:
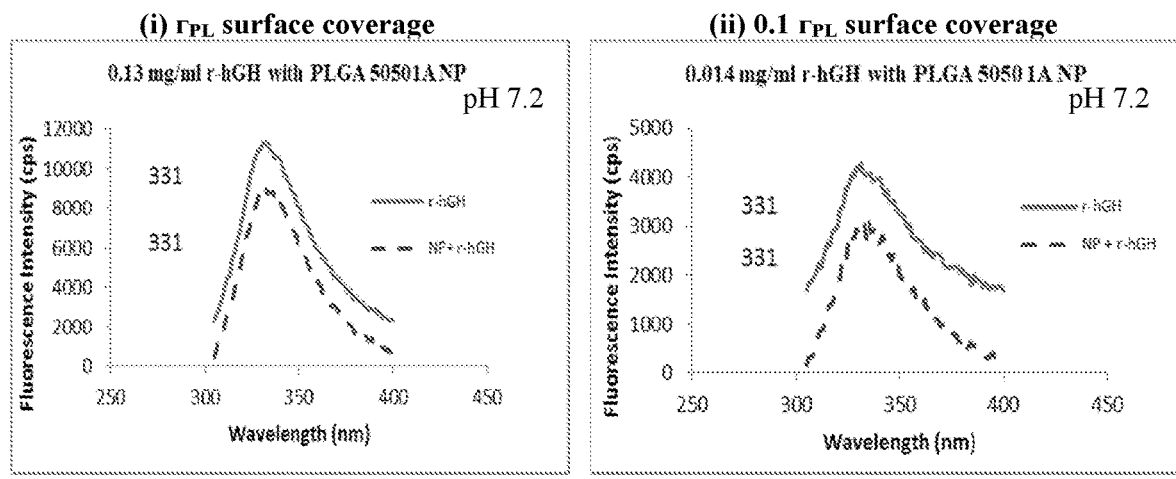
FIGS. 6A-6C are a set of graphs illustrating fluorescence emission spectra of r-hGH before adsorption (–) and after adsorption ( . . . ) onto negatively charged PLGA 5050 1A nanoparticles in 10 mM ionic strength buffer, at pH 7.2 (FIG. 6A), pH 5.3 (FIG. 6B), and pH 4.0 (FIG. 6C).
Figure 6B:
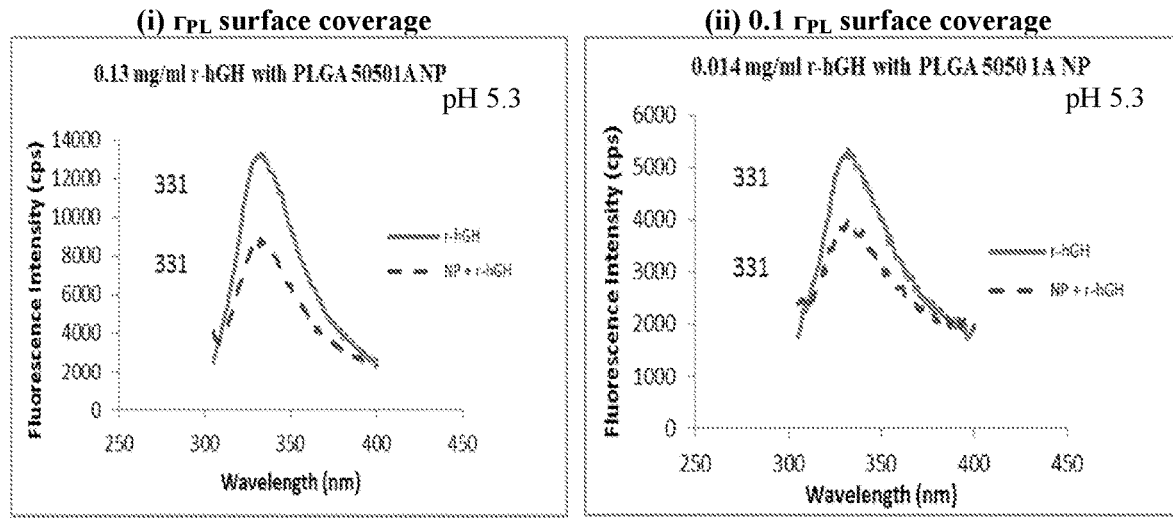
Figure 6C:
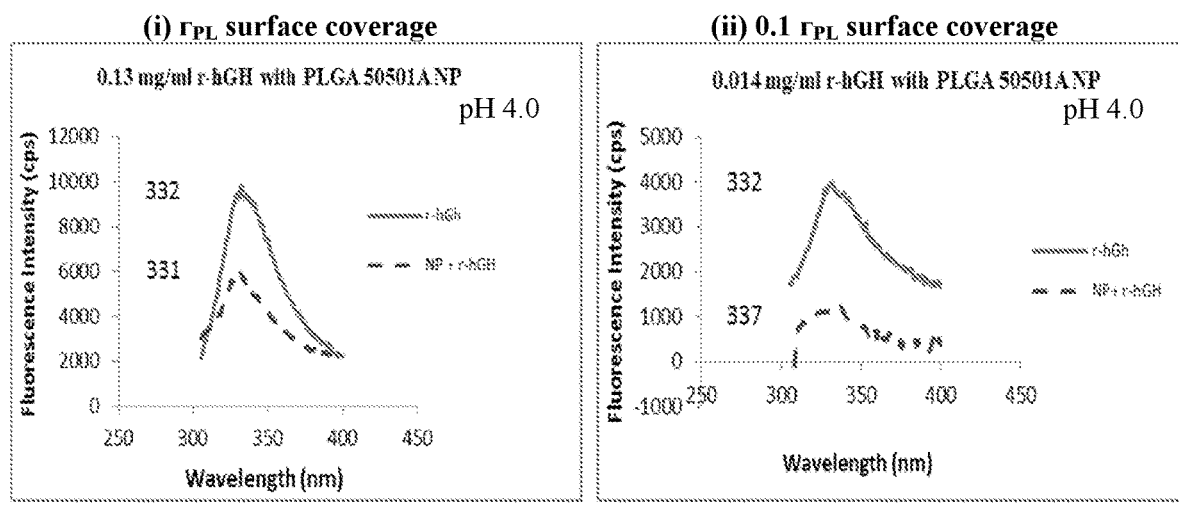
Figure 7A:
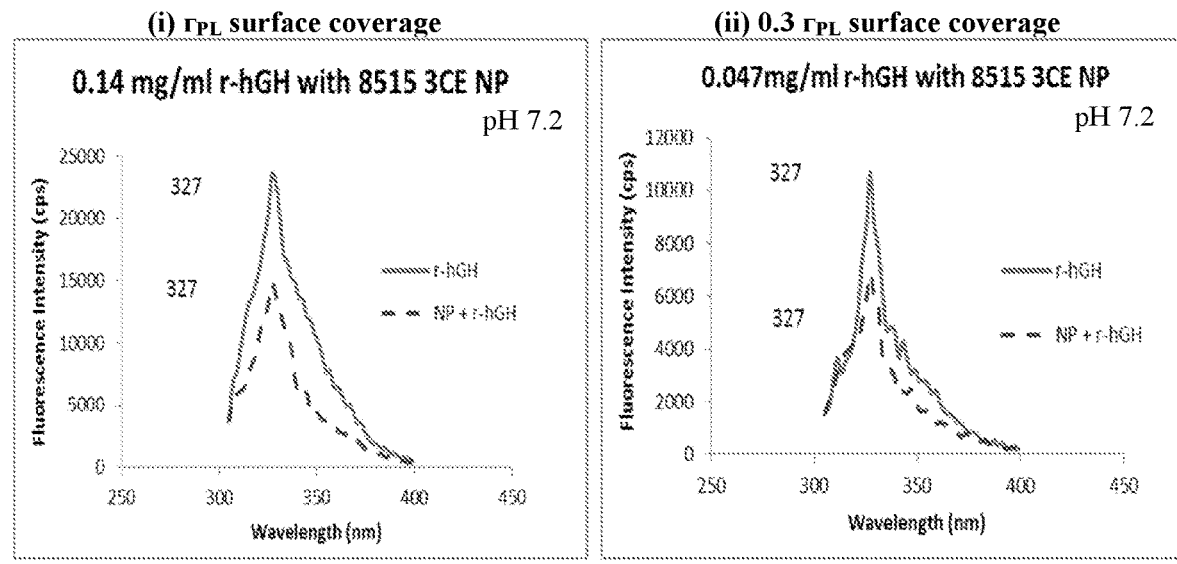
FIGS. 7A-7B are a set of graphs illustrating fluorescence emission spectra of r-hGH before adsorption (–) and after adsorption ( . . . ) onto negatively charged PLGA 8515 3CE nanoparticles in 10 mM ionic strength buffer at pH 7.2 (FIG. 7A) and pH 5.3 (FIG. 7B).
Figure 7B:
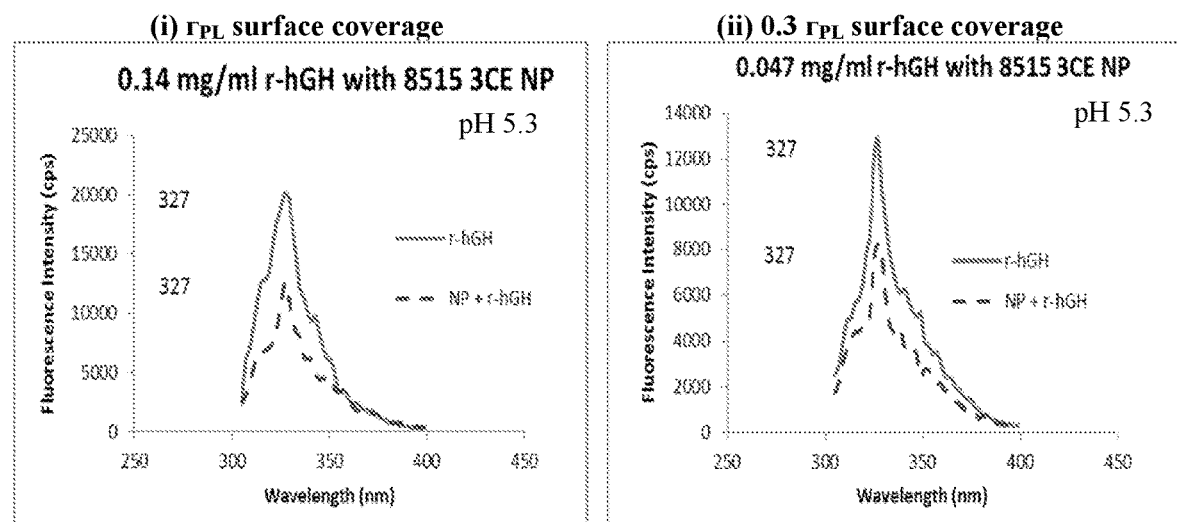
Figure 8A:
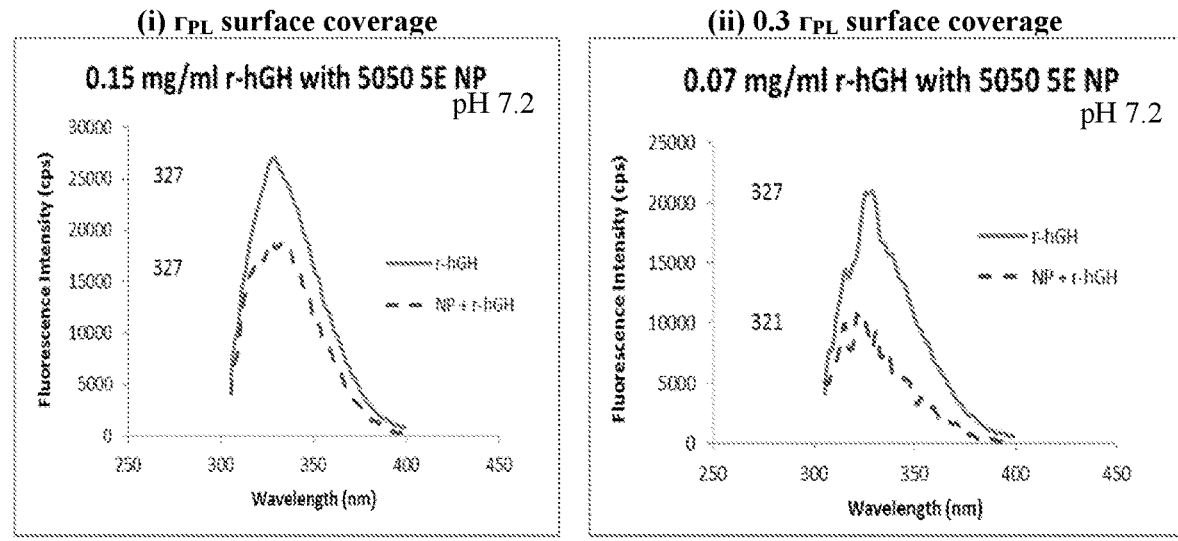
FIGS. 8A-8B are a set of graphs illustrating fluorescence emission spectra of r-hGH before adsorption (–) and after adsorption ( . . . ) onto negatively charged PLGA 5050 5E nanoparticles in 10 mM ionic strength buffer at pH 7.2 (FIG. 8A) and pH 5.3 (FIG. 8B).
Figure 8B:
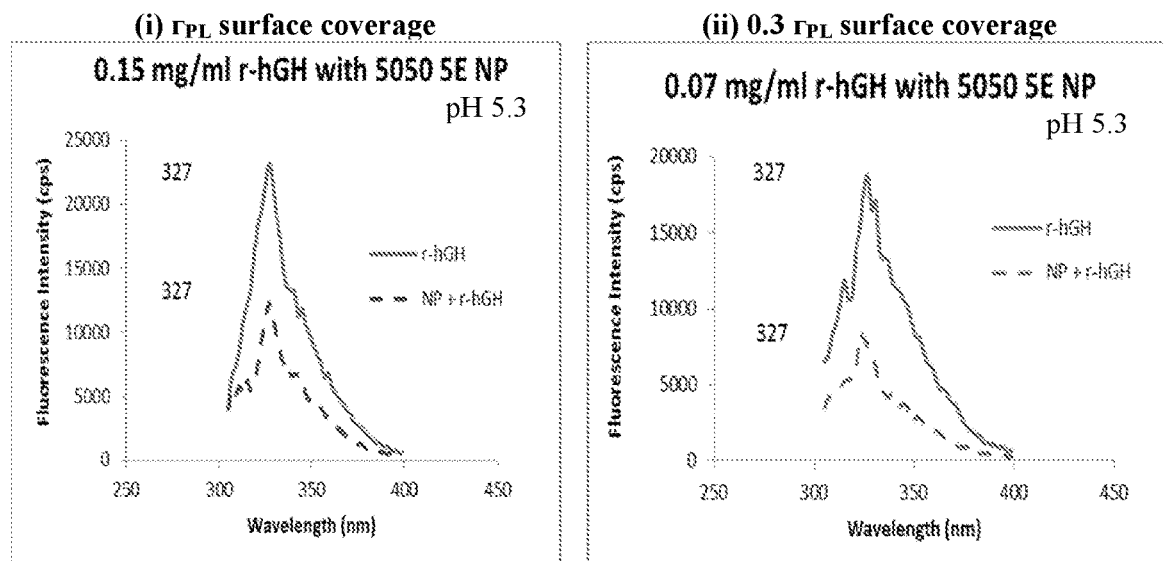

The three dimensional structure of r-hGH with the hydrophobic environment of tryptophan is depicted in FIG. 5. Changes in fluorescence emission spectra of r-hGH when adsorbed on the different polymer nanoparticles as a function of varying pH conditions are depicted in FIGS. 6A-6C, 7A-7B, and 8A-8B. The fluorescence intensity for adsorbed protein is shown relative to the protein in solution. The emission maximum and quantum yield of tryptophan residues in proteins can vary greatly and the variation is due to the three dimensional structure of the proteins. FIGS. 6A-6C shows that the wavelength of maximum emission of r-hGH in solution was independent of pH (4.0, 5.3, and 7.2) irrespective of the protein concentration. Table III presents the shifts in the emission maximum and the changes in Fluorescence spectroscopy is suitable to study the conformation of the r-hGH molecule, as its single tryptophan residue (Trp 86) is buried in the hydrophobic interior and is involved in a hydrogen bond with an aspartic acid residue (Asp 169), located in another α-helix strand. FIG. 5 depicts the crystal structure of r-hGH, with a blowup of the environment of the single tryptophan of the molecule. The tyrosine is buried just under the surface. Tryptophan is surrounded by nonpolar amino acids with the exception of Lys145 and Asp 169. This moderately hydrophobic environment is consistent with the emission maximum. As the tryptophan environment moves toward hydrogen-bonding groups and/or becomes exposed to water, their emission is known to shift to longer wavelengths.

Without intending to be limited to any particular theory, the results in Table III suggest that the decrease in fluorescence quantum yield can be explained by electron transfer quenching by, for instance, the local peptide carbonyl group or by neighboring amino acid side chains. Fluorescence intensity is sensitive to local environment of the tryptophan residue and affected by several factors such as solvent polarity, excited state electron or proton transfer, the amide groups of glutamine and asparagine, the carboxyl groups of glutamic and aspartic acids, lysine-amino group, tyrosine phenol, cysteine sulfhydryl, and histidine imidazole. Excited-state proton transfer is the best characterized non-radiative process. Three excited-state proton transfer reactions occur, depending on the availability of strong proton donors or acceptors. Below pH 4.0, the fluorescence is quenched by acid-catalyzed protonation of the indole ring with pKa about 2-3 and above pH 11 the fluorescence is quenched by base-catalyzed deprotonation of indole NH with pKa about 12-13. At intermediate pH the fluorescence is quenched by proton exchange at indole C2, C4, and C7. Exchange also occurs at C3 in indole compounds with a hydrogen at this position. Proton exchange at aromatic carbons on the excited indole ring is catalyzed by good proton donors.

Overall, interaction of r-hGH with 5050 1A nanoparticles shows lowest quenching at pH 5.3 and 7.2, followed by 8515 3 CE nanoparticles at pH 5.3 and 7.2 while 5050E NPs shows highest quenching at all pH conditions. Increase in quenching in order of PLGA 5050 5E>PLGA 8515 3CE>50501A at a given pH shows effect of surface of hydrophobicity of the polymer and this can be supported by the fact that decrease in intensity can be due to change in tryptophan environment, alkylated surface, anionic (—COO⁻) groups on the polymer surface or shielding of r-hGH fluorescence by the nanoparticles due to increases in interaction. Red shift at pH 4.0 for 5050 1A nanoparticles showing tryptophan exposure to polar surface and blue shift at pH 7.2 for 5050 5E nanoparticles showing tryptophan exposure to apolar environment indicates conformational changes in structure of r-hGH, additional analysis by circular dichroism is required to evaluate the conformation changes in tertiary structure of r-hGH under all other conditions.

Example 4: Circular Dichroism Spectroscopy

Figure 9A:
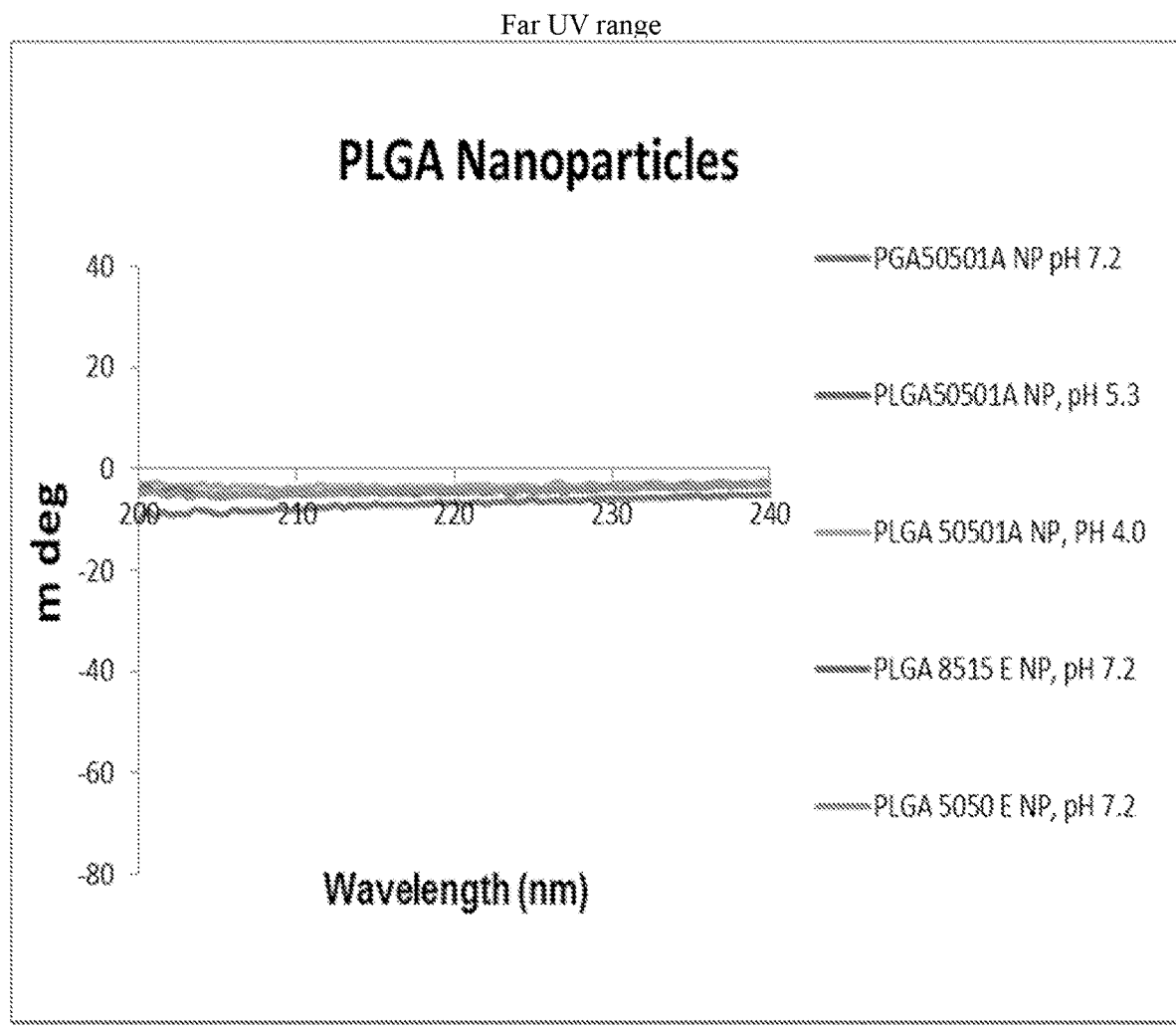
FIGS. 9A-9B illustrates a representative raw CD signal for PLGA nanoparticle dispersions in the far UV (FIG. 9A) scan range and near UV (FIG. 9B) scan range as a function of pH.
Figure 9B:
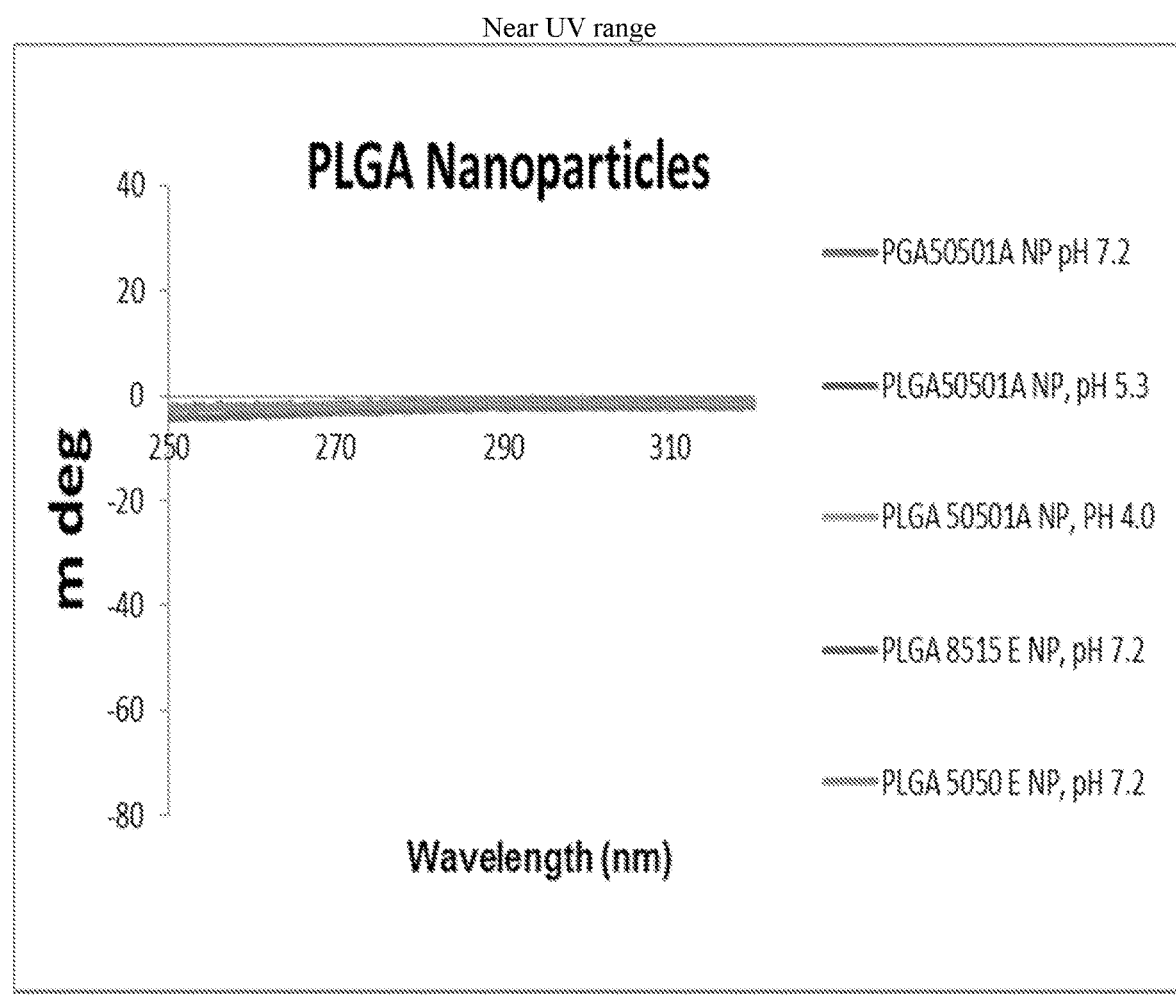

PLGA 50501A nanoparticles in pH 7.2, 5.3 and 4.0, PLGA 8515 3CE nanoparticles in pH 7.2 and PLGA 5050 5E nanoparticles in pH 7.2 were used to evaluate structural changes in r-hGH upon adsorption using CD. Because PLGA 8515 3CE and 5050 5E nanoparticles were not stable in pH 4.0 buffer media and resulted in particle aggregation at pH 5.3 in presence of r-hGH, these nanoparticles were not used for CD study. The spectra for PLGA nanoparticles in each buffer system in far and near UV range are depicted in FIG. 9 to account for any interference.

r-hGH in Solution

Figure 10:
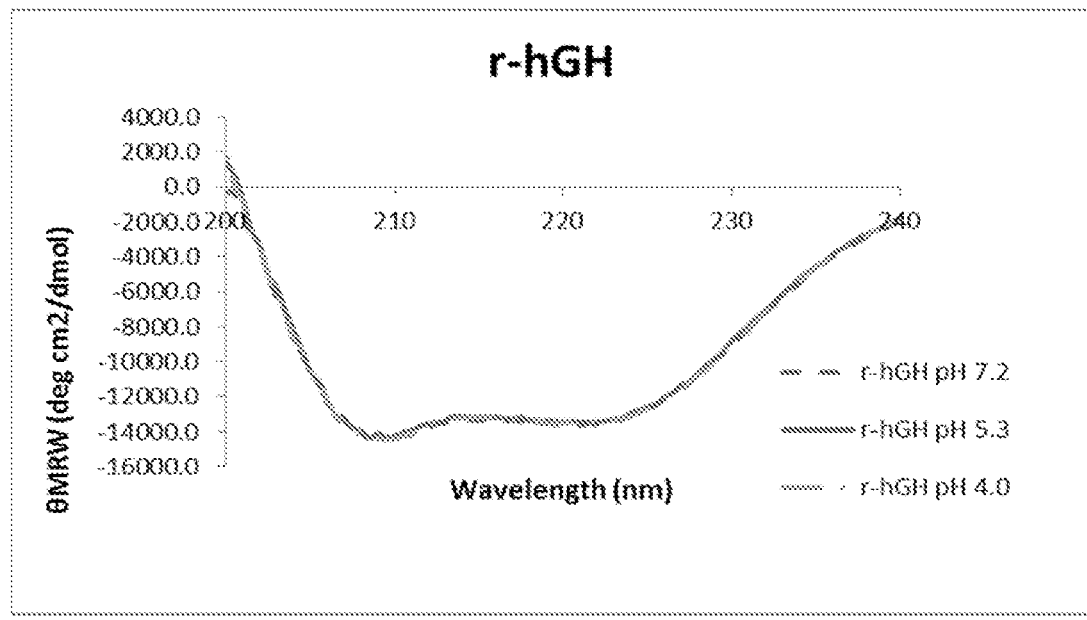
FIG. 10 is a graph illustrating comparison of far-UV spectra of free r-hGH in solution and those adsorbed onto PLGA 5050 1A particles as a function of solution pH.

The CD scans for r-hGH solutions revealed two negative bands at 222 nm and 209 nm with the band intensity at 209 nm stronger than that at 222 nm (FIG. 10). The band at 222 nm is assigned to n-π* amide bond transition while the band at 209 nm is assigned to π-π* transition. The observed CD spectrum of r-hGH with a stronger 209-nm band than the 222-nm band could be attributed to presence of predominantly helical and random coil structures. The helical contents estimated based on absolute ellipticity values were approximately 40% and 33% at 222 and 209 nm respectively in the pH range studied. The α-helix contents estimated based on software analysis were comparable to those obtained using the absolute ellipticity values (Table IV).

tryptophan since other chromophores such as the amide bond, phenylalanine and tyrosine are not known to contribute to dichroism in this region. The intensity of the 294 nm peak decreased at pH 4.0 and 5.3 compared with that for pH 7.2. In a thermal unfolding study using near UV circular dichroism, unfolding of r-hGH was previously shown to be due to loss of positive dichroism. While the reduction in positive dichroism is not significant under these conditions, these results suggest that the conformational stability of r-hGH may be lower at low pH (<4.0).

r-hGH Adsorption on to PLGA Surface

Figure 12A:
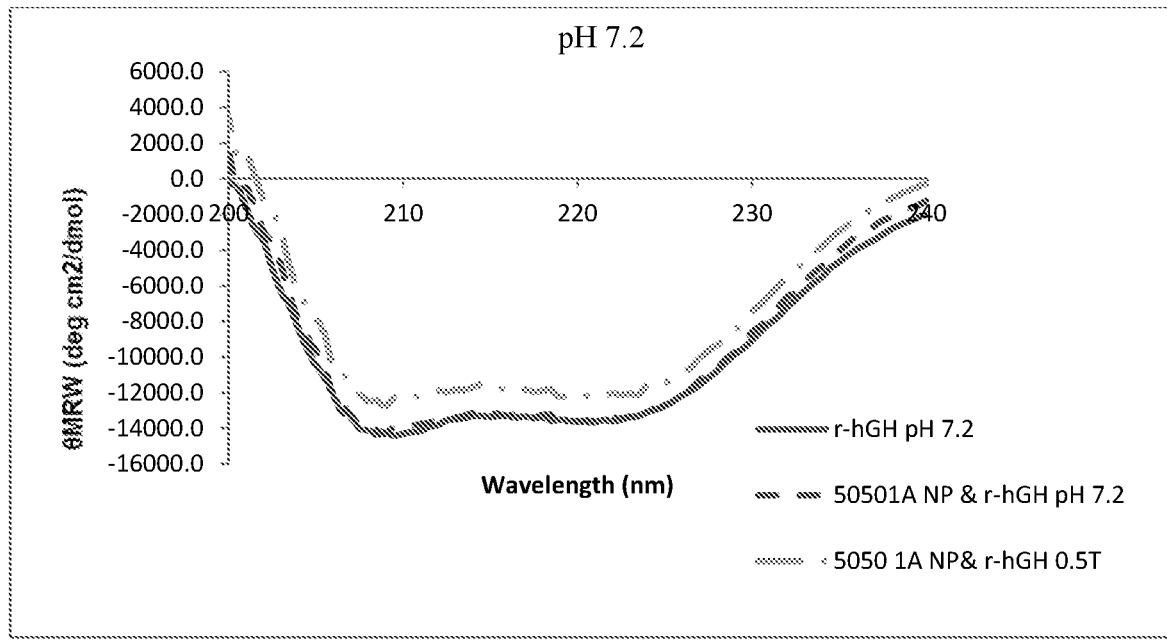
FIGS. 12A-12C are a set of graphs illustrating comparison of far-UV spectra of free r-hGH in solution and those adsorbed onto PLGA 5050 1A particles as a function of solution pH 7.2 (FIG. 12A), pH 5.3 (FIG. 12B), and pH 4.0 (FIG. 12C).
Figure 12B:
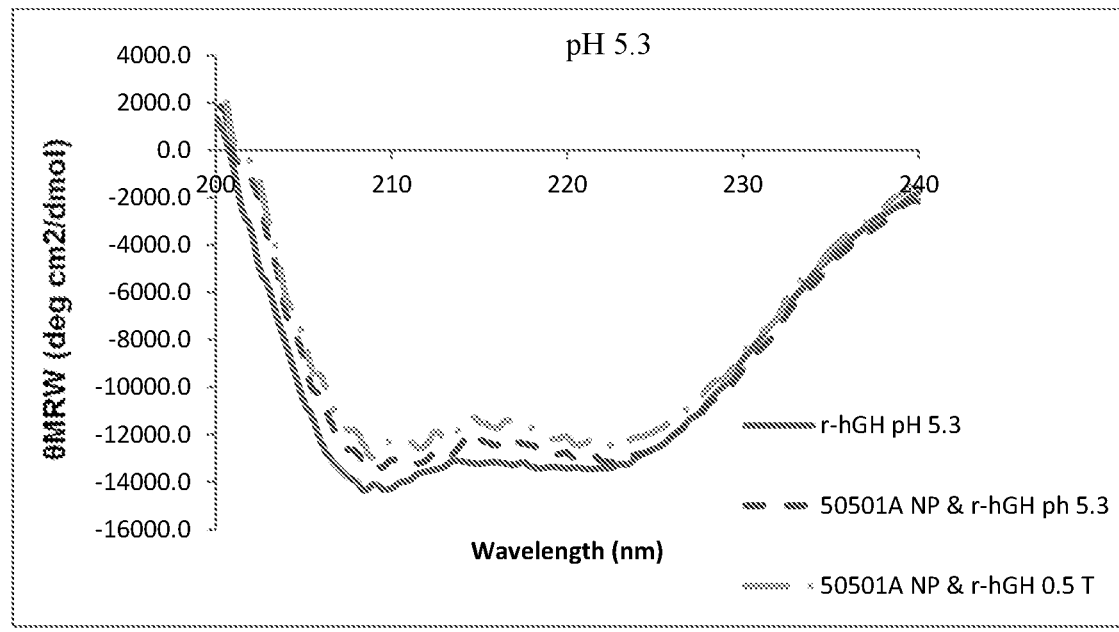
Figure 12C:
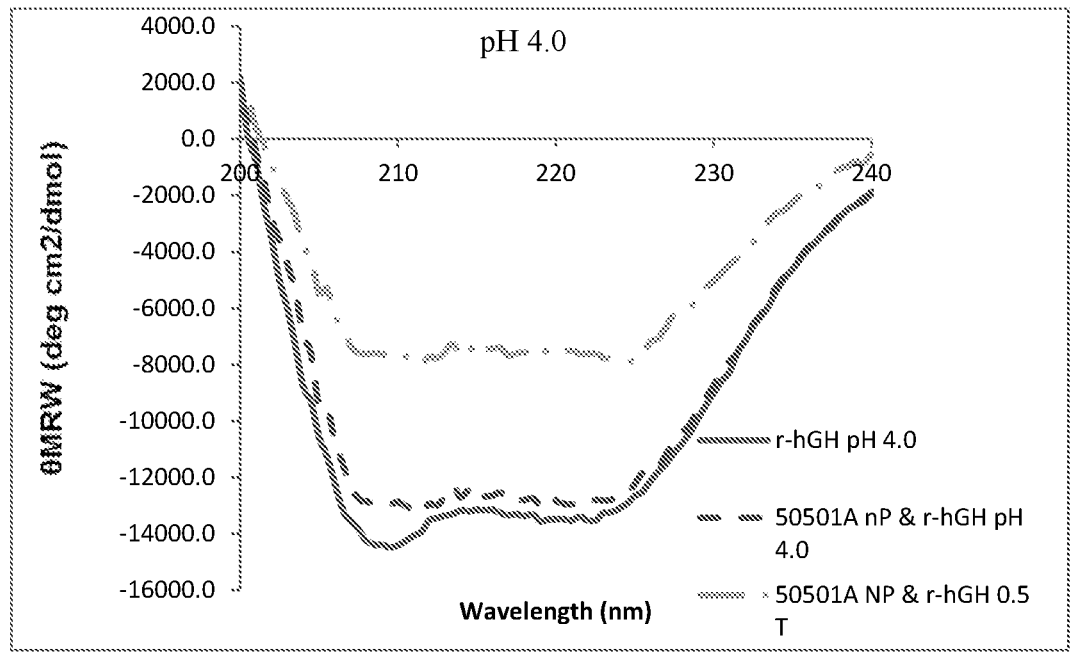
Figure 13:
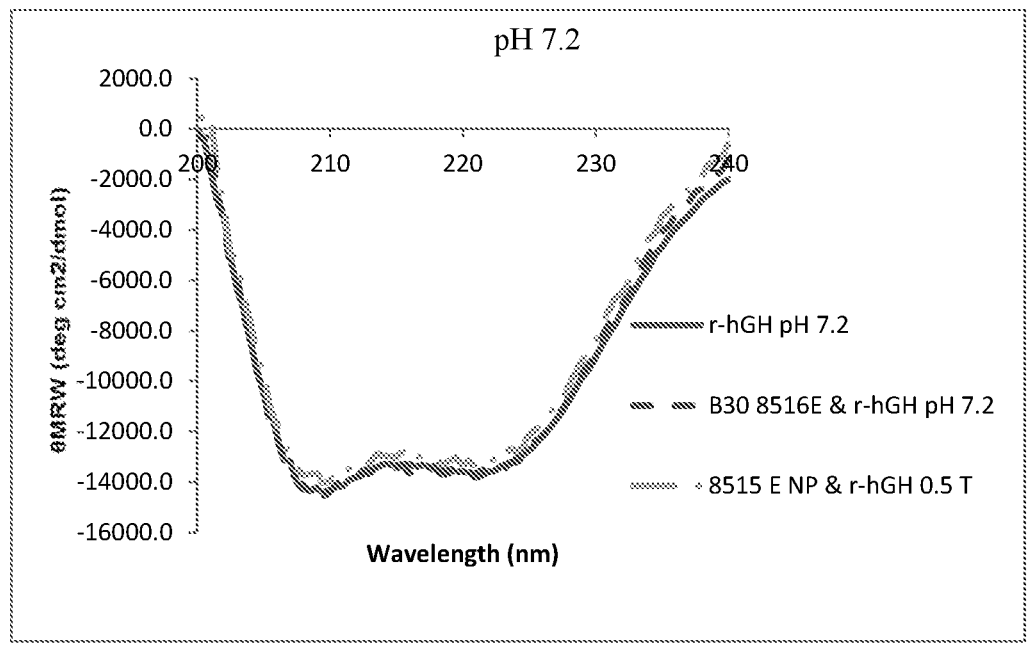
FIG. 13 is a graph illustrating comparison of far-UV spectra of free r-hGH in solution and those adsorbed onto PLGA 8515 3CE particles as a function of solution pH.
Figure 14:
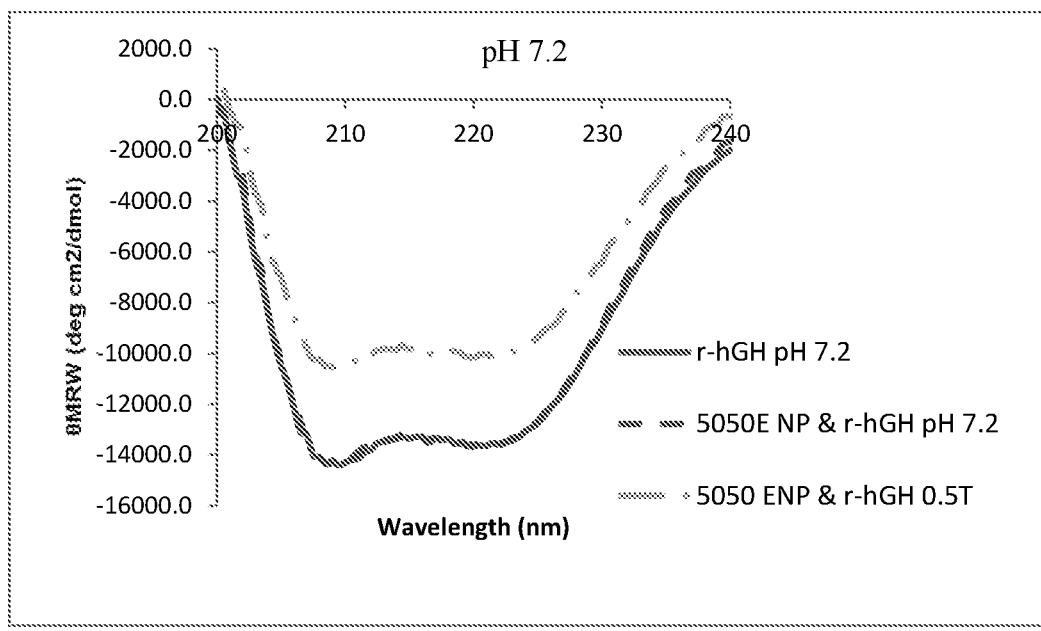
FIG. 14 is a graph illustrating comparison of far-UV spectra of free r-hGH in solution and those adsorbed onto PLGA 5050 5E particles as a function of solution pH.

The far-UV spectra of r-hGH in solution and that adsorbed onto negatively charged PLGA 50501A are depicted in FIGS. 12A-12C for pH 7.2, 5.3 and 4.0 respectively. The spectra for r-hGH in solution and that adsorbed onto ester end capped PLGA 8515 3CE and PLGA 5050 5E in pH 7.2 are depicted in FIG. 13 and FIG. 14 respectively. The CD spectra scans at pH 7.2 showed no change in secondary structure of r-hGH adsorbed onto all three types of PLGA nanoparticles at full surface coverage while that at lower surface coverage showed a change in spectral pattern with a loss in a-helix structure for PLGA 5050 5E nanoparticles. The CD spectra obtained at full surface coverage of r-hGH adsorbed on to uncapped PLGA 50501A nanoparticles at pH 5.3 and pH 4.0 showed some loss of band intensity at 209 nm and overall minimal changes in secondary structure (FIGS. 112B-12C, (Table IV). The CD data for low surface coverage of adsorbed r-hGH onto PLGA 50501A at pH 4.0 showed a red shift of band at 222 nm (225 nm) and significant reduction in band intensity with an overall strong reduction in a-helix character while CD data at low surface coverage onto PLGA 50501A at pH 5.3 showed some loss of band intensity and minimal change in secondary structure.

Figure 15A:
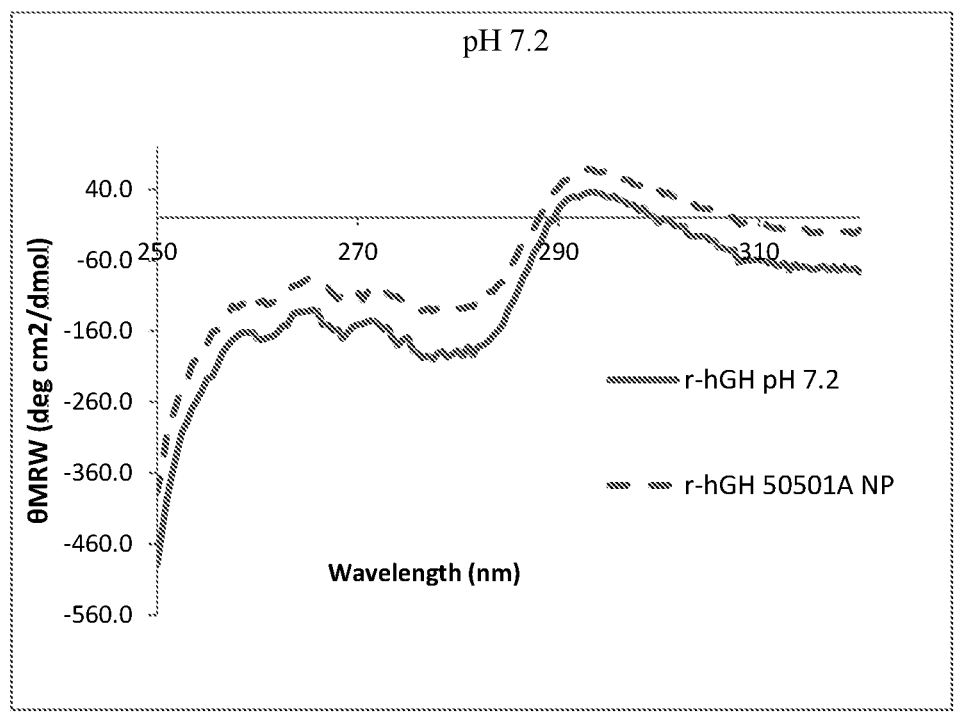
FIGS. 15A-15C are a set of graphs illustrating comparison of near-UV spectra of free r-hGH in solution and those adsorbed onto PLGA 5050 1A particles as a function of solution pH 7.2 (FIG. 15A), pH 5.3 (FIG. 15B), and pH 4.0 (FIG. 15C).
Figure 15B:
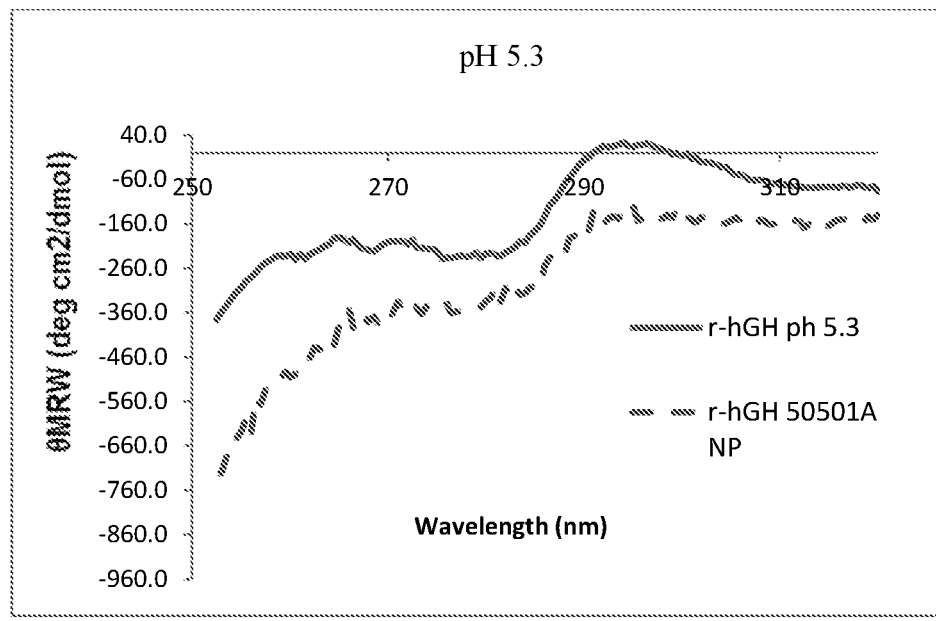
Figure 15C:
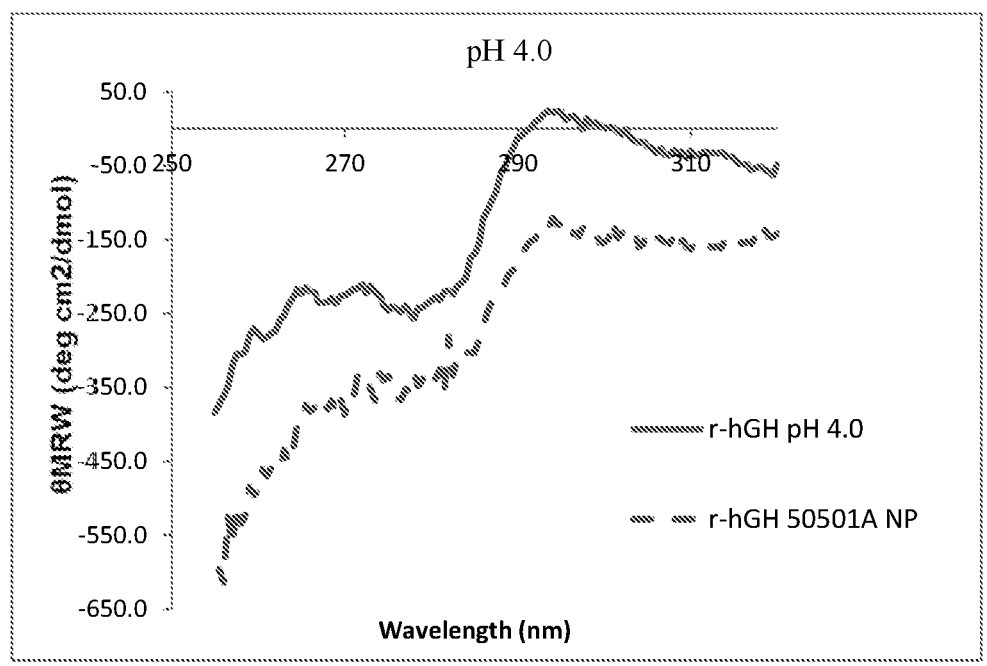

Due to lack of polymer stability upon adsorption, the near-UV scans of adsorbed r-hGH samples were evaluated under limited conditions. The near-UV scans of r-hGH adsorbed onto PLGA 50501A nanoparticles in comparison to that for r-hGH in solution at pH 7.2, 5.3 and 4.0 are shown in FIGS. 15A-15C respectively whereas these comparative scans for PLGA 8515 3CE and PLGA 5050 5E with r-hGH

TABLE IV

Comparison of % α helix in r-hGH solution and r-hGH adsorbed on PLGA Nanoparticles

| pH Sample | % α helix [Θ]222 | % α helix [Θ]209 | % α helix CONTIN and CDSSTR | % β sheet CONTIN and CDSSTR |
|---|---|---|---|---|
| 7.2 r-hGH solution | 40.63 | 33.72 | 41 | 4 |
| 5.3 r-hGH solution | 40.20 | 33.58 | 43 | 3 |
| 4.0 r-hGH solution | 40.37 | 33.92 | 49 | 3 |
| 7.2 r-hGH - PLGA 50501A NP (r) | 40.54 | 33.42 | 41 | 4 |
| r-hGH - PLGA 50501A NP (0-5 r) | 37.08 | 29.08 | 40 | 4 |
| 5.3 r-hGH - PLGA 50501A NP (r) | 39.69 | 30.90 | 39 | 3 |
| r-hGH - PLGA 50501A NP (0-5 r) | 38.38 | 29.78 | 38 | 4 |
| 4.0 r-hGH - PLGA 50501A NP (r) | 39.18 | 29.92 | 43 | 6 |
| r-hGH - PLGA 50501A NP (0.5 r) | 27.96 | 14.99 | 31 | 12 |
| 7.2 r-hGH - PLGA 8515 3CE NP (r) | 41.00 | 34.08 | 41 | 3 |
| r-hGH - PLGA 8515 3CE NP (0.5 r) | 39.36 | 31.73 | 40 | 3 |
| 7.2 r-hGH - PLGA 5050 5E NP (r) | 40.61 | 33.67 | 40 | 4 |
| r-hGH - PLGA 5050 5E NP (0.5 r) | 32.77 | 23.01 | 33 | 8 |

Figure 11:
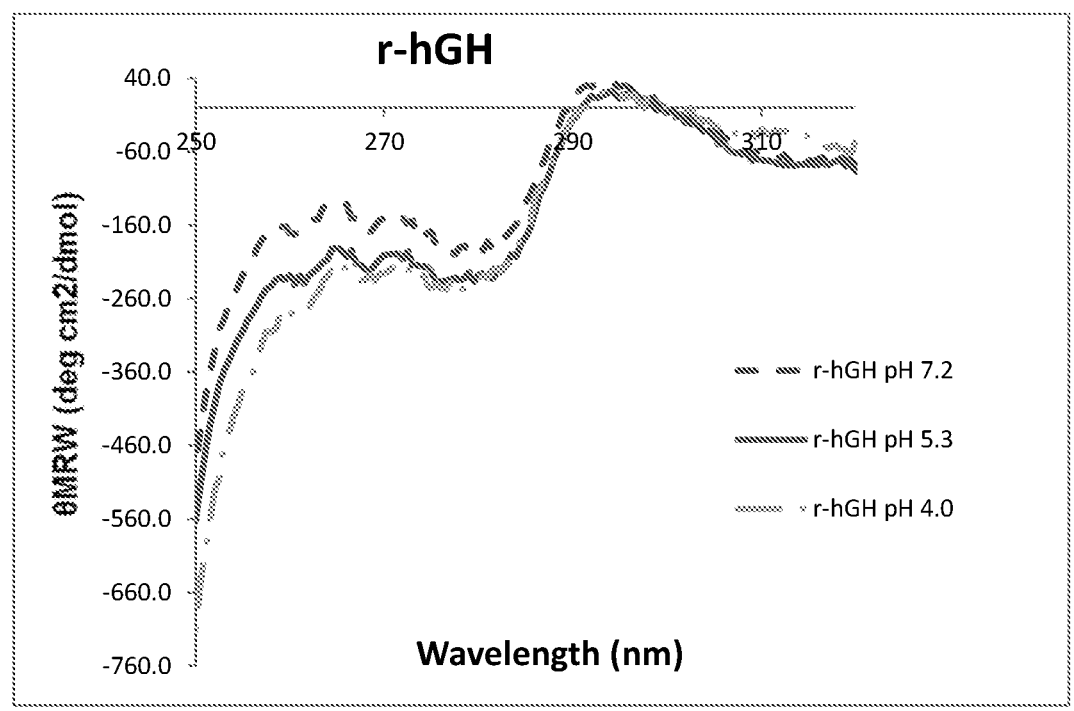
FIG. 11 is a graph illustrating near UV spectra of r-hGH as a function of pH.
Figure 16:
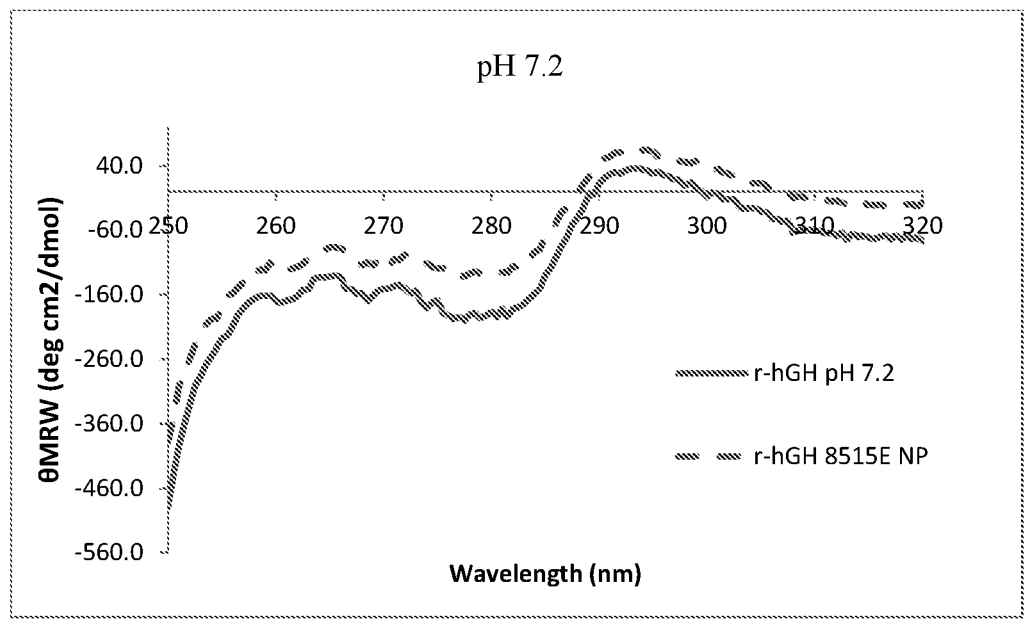
FIG. 16 is a graph illustrating comparison of near-UV spectra of free r-hGH in solution and those adsorbed onto PLGA 8515 3CE particles as a function of solution pH.
Figure 17:
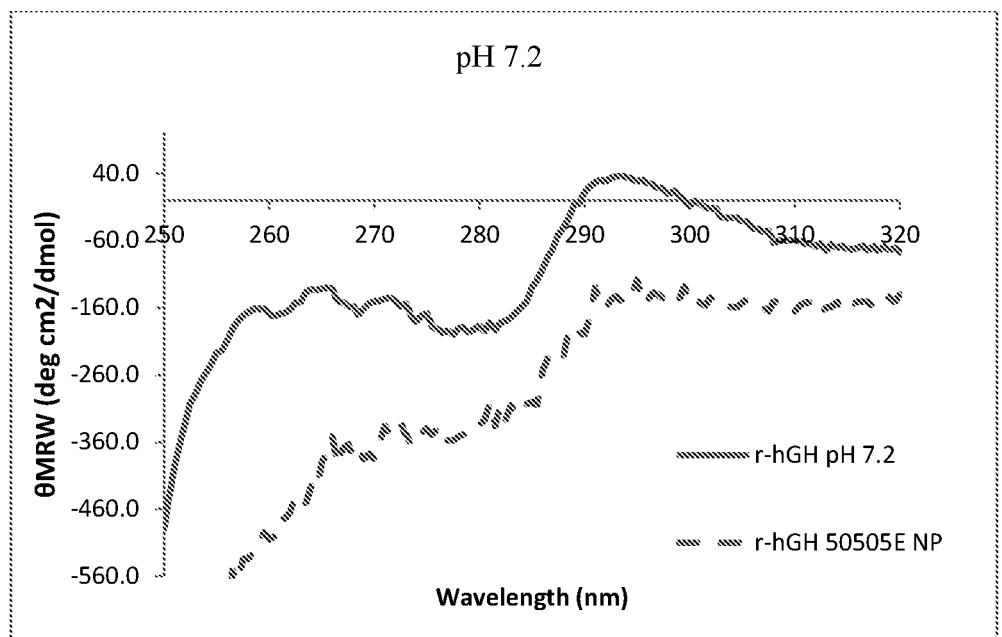
FIG. 17 is a graph illustrating comparison of near-UV spectra of free r-hGH in solution and those adsorbed onto PLGA 5050 5E particles as a function of solution pH.

The near-UV spectra of r-hGH in solution as a function of pH are presented in FIG. 11. Regardless of the pH studied, the tertiary spectra of r-hGH in solution revealed 3 negative bands in the 255-270 nm range, attributed to phenyl alanine. The large positive dichroism above 294 nm is attributed to in solution at pH 7.2 are depicted in FIG. 16A and FIG. 17A respectively. The results from near-UV scan for r-hGH adsorbed onto PLGA particles demonstrated the loss of positive dichroism at 294 nm along with reduction in intensity of three negative bands between 255-275 nm for interaction with PLGA 5050 1A particles at pH 5.3 and 4.0 indicating rearrangements in tertiary structure. At pH 7.2, interaction of r-hGH with PLGA 5050 1A and PLGA 8515 3CE did not show significant changes in near UV spectra indicating tertiary structure stability while that with PLGA 5050 5E demonstrated structural rearrangement in r-hGH upon adsorption under this condition.

Evaluation of Secondary Structure

Without intending to be limited to any particular theory, it is possible that the adsorption of r-hGH onto PLGA is primarily driven by hydrophobic interactions in addition to favorable electrostatic interactions (attraction). The presence of electrostatic repulsion between protein and PLGA or between adsorbed protein molecules could induce structural changes. In addition, structural changes may occur due to low conformational stability of protein in solution. In spite of the similar nature of electrostatic interaction (repulsion) between all three grades of PLGA and r-hGH, differences were noted in structural changes for r-hGH when adsorbed at lower surface coverage on PGA 50501A and 8515 3CE versus 5050 5E nanoparticles at pH 7.2. This can be due to lower magnitude of charge, higher hydrophobicity and consequently spreading of r-hGH at lower surface coverage. Minimal changes in r-hGH secondary structure upon adsorption at all three types of PLGA nanoparticles are in agreement with the study which has shown that CD spectra of r-hGH released from PLGA microspheres at pH 7.2 maintained monomeric and dimeric form ranging from 70-80%.

r-hGH is known to be most stable at isoelectric point at low concentrations and this supports the minimum changes in structure at high and low surface coverage onto PLGA 5050 1A nanoparticles where surface is least hydrophobic in nature and total surface coverage on these particles is much lower in comparison to PLGA 8515 3CE and PLGA 5050 5E nanoparticles. The observed loss of secondary structure that occurred upon adsorption of r-hGH onto PLGA 5050 1A at pH 4.0, can be due to electrostatic interactions and lower conformational stability of protein at lower surface coverage compared to higher surface coverage.

Evaluation of Tertiary Structure

In general, the near-UV scan for r-hGH adsorbed onto PLGA particles showed loss of positive dichroism above 290 nm for all the conditions studied, suggesting loss of tertiary structure of r-hGH as a result of adsorption, except in the cases of PLGA 5050 1A and PLGA 8515 3CE nanoparticles at pH 7.2. These results are in conformance to the data obtained in fluorescence spectroscopy and DLS study. Without intending to be limited to any particular theory, the entropic gain for r-hGH as a result of unfolding may be a primary driving force for adsorption onto the hydrophobic polymer surface.

Example 5: Isothermal Titration Calorimetry

The Isothermal titration calorimetry determine the binding affinity and the forces involved in the adsorption of r-hGH to a moderately hydrophobic surface as well as assess the changes in protein molecules as a consequence of their association. Due to the instability of PLGA 8515 3CE and PLGA 5050 5E nanoparticles in pH 4.0 media, binding isotherms could not be obtained under these conditions. Moreover, lack of stability of PLGA 8515 3CE and PLGA 5050 5E nanoparticles upon adsorption of r-hGH resulted in a poor binding isotherm at isoelectric pH 5.3 to acquire any thermodynamic parameters for binding. Therefore, effect of pH was studied using PLGA 5050 1A nanoparticles in pH 7.2, 5.3 and 4.0 (FIG. 18), while the effect of polymer grade was studied using PLGA 5050 1A, PLGA 8515 3CE and PLGA 5050 5E nanoparticles at pH 7.2 (FIG. 19A-19C). Additionally, the change in heat capacity was also evaluated for PLGA 5050 1A and r-hGH interaction at all three pH conditions by conducting the experiments at 15° C. (FIG. 20).

Figure 18:
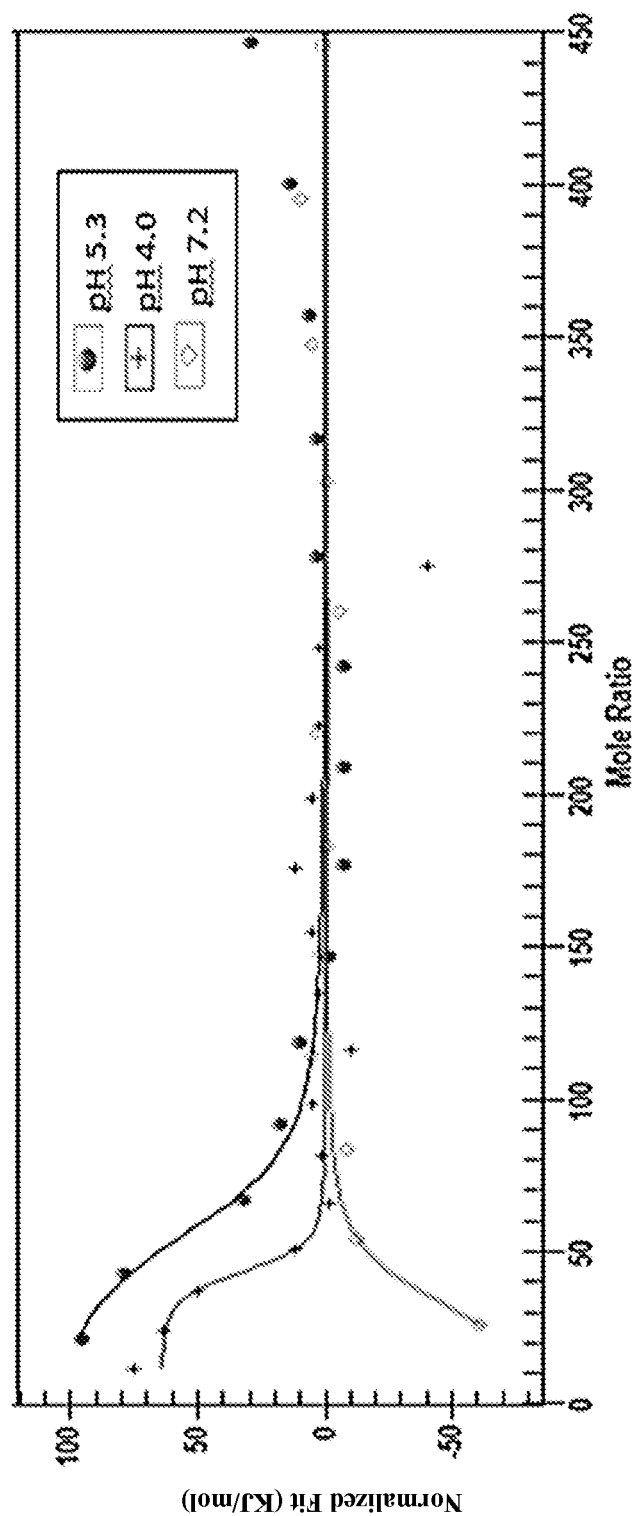
FIG. 18 is a graph illustrating calorimetric data for the binding of r-hGH to negatively charged PLGA 5050 1A across pH 7.2, 5.3 and 4.0 at 25° C. Integrated data for the titration after subtraction of control.
Figure 19A:
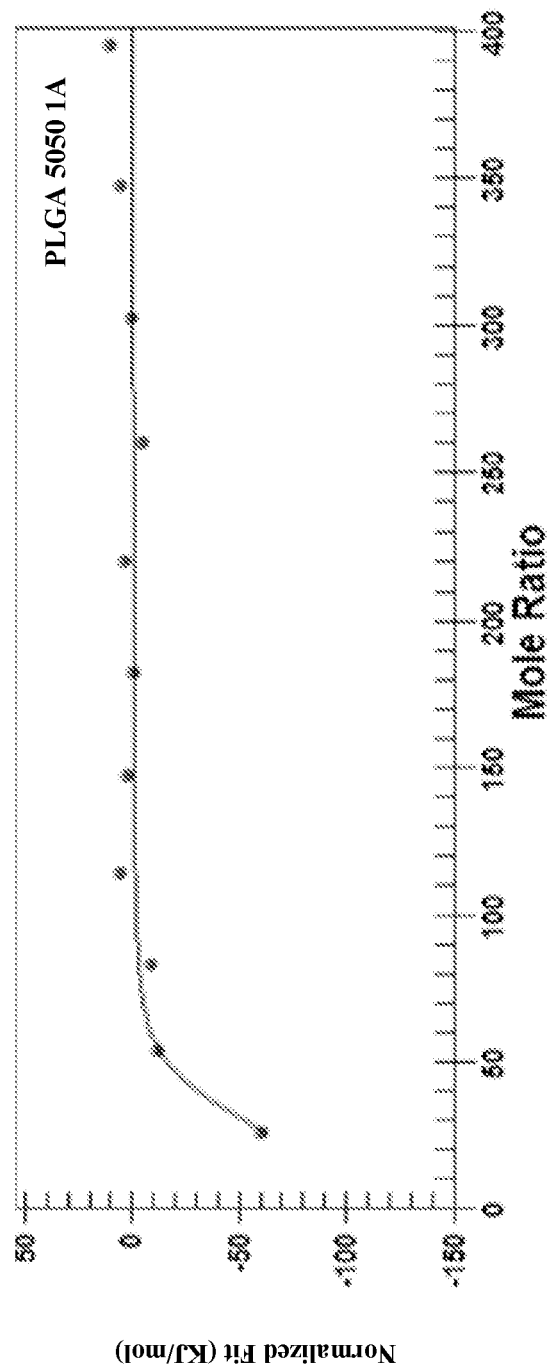
FIGS. 19A-19C are set of graphs illustrating calorimetric data for the binding of r-hGH to negatively charged (FIG. 19A) PLGA 5050 1A, (FIG. 19B) 8515 3CE and (FIG. 19C) PLGA 5050 5E at pH 7.2 and 25° C. Integrated data for the titration after subtraction of control.
Figure 19B:
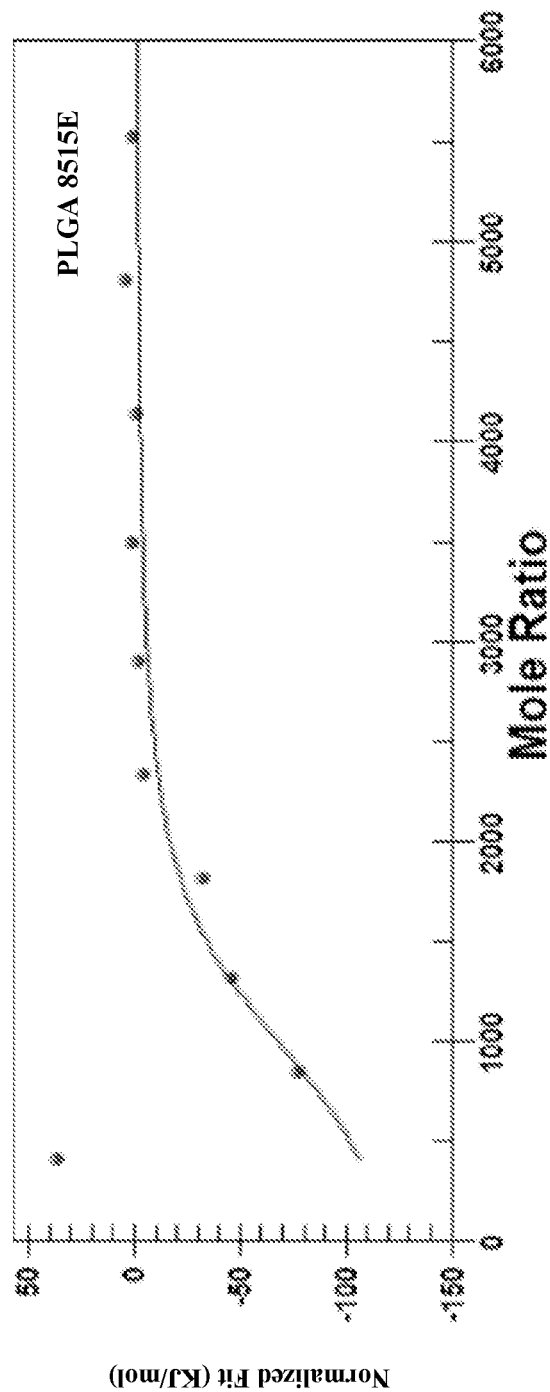
Figure 19C:
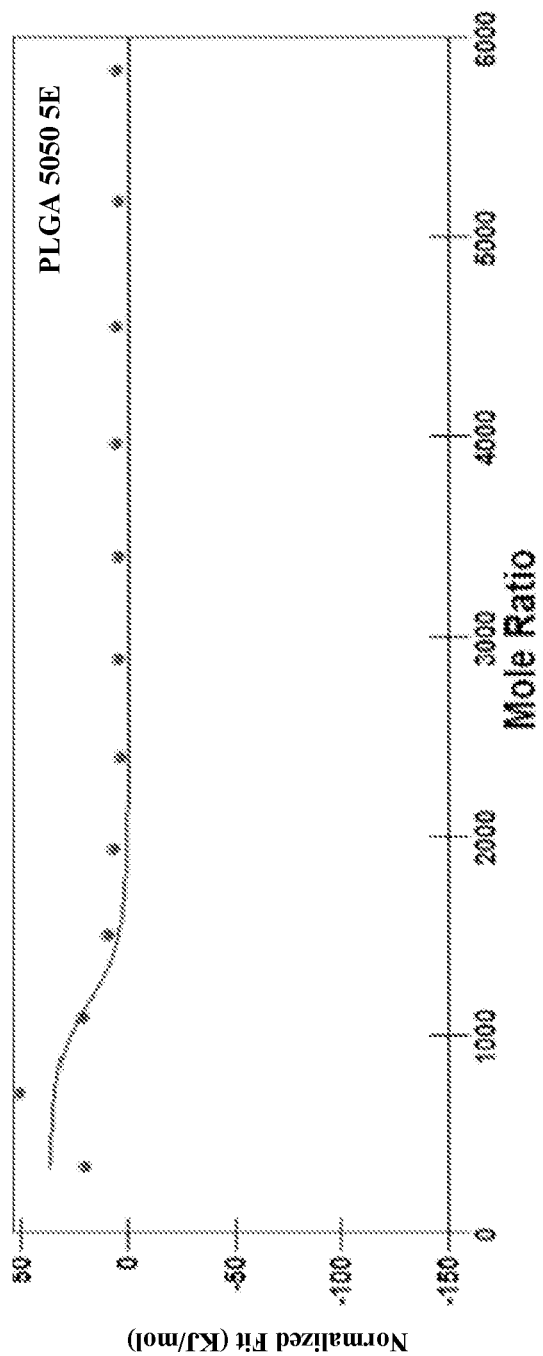
Figure 20:
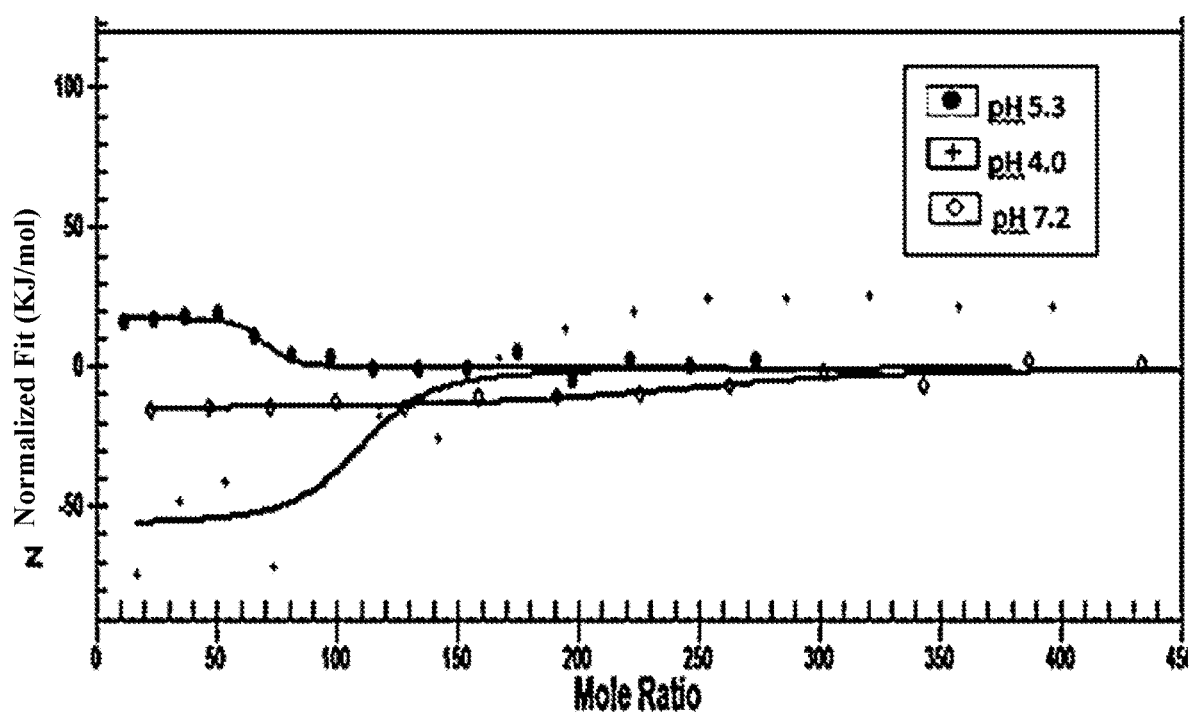
FIG. 20 is a graph illustrating calorimetric data for the binding of r-hGH to negatively charged PLGA 5050 1A across pHs 7.2, 5.3 and 4.0 at 15° C. Integrated data for the titration after subtraction of control.

During the titration with PLGA nanoparticle suspension in the cell and r-hGH sequential injections from the syringe, the heats of binding were integrated and a titration plot of heat released per injection versus the molar ratio of r-hGH to PLGA were plotted as shown in FIGS. 18-20. Each data set was corrected for respective heats of dilution, measured in separate control experiments. The solid lines in in FIGS. 18-20 is the nonlinear fit to the data assuming a single-site binding model. The interaction of protein with PLGA 5050 1A and PLGA 8515 3CE nanoparticles was found to be strongly exothermic at pH 7.2 (FIGS. 18 and 19B, respectively) while endothermic at pH 5.3 and 4.0 (FIG. 18) with PLGA 5050 1A and pH 7.2 (FIG. 19C) with PLGA 5050 5E. The thermodynamic parameters are summarized in Table V. The change in enthalpy (ΔH) values was found to be largely negative at pH 7.2 while positive at pH 5.3 and 4.0. (ΔH=−94.2, 363.3 and 110.5 kJ/mol of injectant for pH 7.2, 5.3 and 4.0 respectively) for PLGA 5050 1A nanoparticles. The change in enthalpy (ΔH) for interaction with 8515 3CE nanoparticles was −111.7 kJ/mol and that for interaction with 5050 5E nanoparticles was 36.67 kJ/mol.

TABLE V

Thermodynamic parameters for the binding of rhGH to PLGA nanoparticles in 10 mM ionic strength buffer, 25° C. as a function of pH (n = 3).

| Thermodynamic parameter | 5050 1A pH 7.2 | | 5050 1A pH 5.3 | | 5050 1A PH 4.0 | |
|---|---|---|---|---|---|---|
| | Average | STDEV | Average | STDEV | Average | STDEV |
| Kd (M) | 1.81E−07 | 2.1E−07 | 3.21E−06 | 4.1E−06 | 2.98E−08 | 2.90E−09 |
| n | 22.0 | 3 | 42.50 | 9.69 | 37.01 | 0.91 |
| ΔH (kJ/mol) | −94.2 | 21 | 363.25 | 35.29 | 110.5 | 18.46 |
| ΔS (kJ/mol) | −182.0 | 84.64 | 493.99 | 110.28 | 514.9 | 61.73 |
| ΔG (J/mol · K) | −39.9 | 4.17 | −33.55 | 5.38 | −42.90 | 4.03 |
| Ka (M$^{-1}$) | 1.79E+07 | 2.1E+07 | 1.83E+06 | 2.4E+06 | 3.36E+07 | 5.93E+04 |
| No. of r-hGH/μm$^2$ of nanoparticles | 4.38E+03 | — | 5.46E+03 | — | 7.38E+03 | — |

TABLE V-continued

Thermodynamic parameters for the binding of rhGH to PLGA nanoparticles in 10 mM ionic strength buffer, 25° C. as a function of pH (n = 3).

| Thermodynamic parameter | 8515 3CE pH 7.2 | | 5050 5E pH 7.2 | |
|---|---|---|---|---|
| | Average | STDEV | Average | STDEV |
| Kd (M) | 3.56E−07 | 1.819E−07 | 5.87E−08 | 2.7E−08 |
| n | 1041.5 | 6.4 | 1190 | 10 |
| $\Delta H$ (kJ/mol) | −111.7 | 15.6 | 36.67 | 0.64 |
| $\Delta S$ (J/mol · K) | −250.34 | 56.80 | 261.89 | 1.8 |
| $\Delta G$ (kJ/mol) | −36.98 | 1.33 | −41.41 | 1.2 |
| Ka (M$^{-1}$) | 3.23E+06 | 1.65E+05 | 1.90E+07 | 8.68E+06 |
| No. of r-hGN/µm2 of nanoparticles | 5.18E+04 | — | 2.37E+05 | — |

The change in free energy ($\Delta G$) for the associations was found to be approximately the same for all three types of nanoparticles under study conditions (~−39 kJ/mol) and was negative, a requirement for spontaneous biomolecular interactions (Norde, W. et. al, *Polym. Adv. Technol.* 6 518-525 (1994)). The equilibrium binding constant (Ka) of the association were in the order of $10^6$-$10^7$ M$^{-1}$ and indicated a moderate binding affinity for different PLGA nanoparticles under varying conditions of pH. In theory, biomolecular interactions with Ka>$10^8$M$^{-1}$ represent strong binding affinity whereas, Ka<$10^3$ M$^{-1}$ characterizes weak binding affinity (Lee, S. *Department of Biological Sciences, Sungkyunkwan University, Structural and biophysical methods for biological Macromolecules in solution, Suwon, Korea;* 19-26 (June 2016)); Velazquez-Campoy, A. et al. *Methods Mol. Biol.* 261, 35-5(2004)). For PLGA 5050 1A nanoparticles, Ka followed the order of pH 4.0>pH 7.2>pH 5.3. Among different particles, Ka followed the order of 5050 5E>5050 1A>8515 3CE nanoparticles at pH 7.2.

The corresponding change in entropy ($\Delta S$) values were in the order of pH 4.0>5.3>7.2 for PLGA 5050 1A Nanoparticles ($\Delta S$=514.9,493.99 and −182.0 J/mol-K for pH 4.0, 5.3 and 7.2 respectively) indicating that binding was favored entropically for isoelectric pH of 5.3 and pH 4.0, whereas it was enthalpically driven for pH 7.2. The change in entropy ($\Delta S$) for different grades of particles were in order of 5050 5E>5050 1A>8515 3CE indicating the reaction was entropically driven for 5050 5E particles versus enthalpically driven reaction for other two polymer grades.

In theory, the amount of protein adsorbed depends on both the number of adsorption sites on the surface and the packing of molecules into these sites (Jonsson U. L. F. et. al, *J. Colloid Interface Sci.* 117 (1), 127-138(1987)). Apparently n, which represents the number of r-hGH molecules bound per PLGA particle, was determined in the titration calorimetry experiment to be ~37, 42, and 22 at pH 4.0, 5.3 an 7.2, respectively, for PLGA 5050 1A particles, whereas that for PLGA 8515 3CE particles and PLGA 5050 5E at pH 7.2 was 1041 and 1190, respectively. The number of binding sites per PLGA particle, assuming PLGA 5050 1A and 5050 5E nanoparticle mean diameter of 50 nm, a density of 1.31 g/cm$^3$ and r-hGH Stokes diameter ~4 nm (Defelippis M. R, et. al., *Biochemistry* 32, 1555-1562(1993)) was calculated to be ~100, whereas that for 8515 3CE was ~400 considering mean particle diameter of 80 nm. Thus, n was found to be within the theoretically ascertained number for PLGA 5050 1A nanoparticles under all pH conditions, whereas it was higher for other two grades of PLGA showing possibility for multilayer adsorption as observed by the DLS study results at these conditions. Accordingly, number of r-hGH molecules per µm$^2$ of PLGA nanoparticles calculated based on n are also presented in Table V. This was 8.46×$10^3$, 7.38×$10^3$ and 4.38×$10^3$ for PLGA 5050 1A nanoparticles at pH 7.2, 5.3 and 4.0 respectively. A very high surface coverage of 2.37× $10^5$ was observed for PLGA 5050 5E nanoparticles followed by 5.18×$10^4$ at PLGA 8515 3CE nanoparticles. FIG. 20 represent the calorimetric data for interaction of r-hGH with PLGA 5050 1A nanoparticles at pH of 7.2, 5.3 and 4.0 at 15° C. The reaction is exothermic at pH 7.2 and endothermic at pH 5.3 similar to reaction at 25° C. However, reaction is observed to be exothermic at pH 4.0 at this temperature condition as opposed to endothermic reaction at 25° C. Thermodynamic parameters for these set of experiments are denoted in Table VI. All three reactions are observed to be spontaneous reaction with similar values of $\Delta G$. $\Delta H$ followed the order of pH 5.3>pH 7.2>pH 4.0, $\Delta S$ followed the order of pH 5.3>pH 7.2>pH 4.0 and Ka followed the order of pH 5.3>pH 4.0>pH 7.2. Surface coverage was found to be higher at 15° C. in comparison to 25° C. for PLGA 5050 1A polymer grade at all pH conditions studied. Calculation of change in heat capacity, $\Delta C_p$ for each of the pH condition is recorded in Table VII. $\Delta C_p$ was negative for interaction at pH 7.2 whereas it was positive for interaction at pH 5.3 and 4.0.

TABLE VI

Thermodynamic parameters for the binding of rhGH to PLGA nanoparticles in 10 mM ionic strength buffer, 15° C. as a function of pH (n = 3).

| Thermodynamic parameter | 5050 1A pH 7.2 | | 5050 1A pH 5.3 | | 5050 1A pH 4.0 | |
|---|---|---|---|---|---|---|
| | Average | STDEV | Average | STDEV | Average | STDEV |
| Kd (M) | 7.04E−07 | 3.9E−07 | 3.05E−08 | 1.05E−07 | 1.16E−07 | 1.03E−6 |
| n | 254.10 | 57.56 | 60.07 | 6.05 | 100.5 | 2.4 |
| $\Delta H$ (kJ/mol) | −18.29 | 3.71 | 52.21 | 3.27 | −56.36 | 5.93 |
| $\Delta S$ (J/mol · K) | 55.04 | 17.76 | 325.1 | 30.65 | −62.79 | 12.87 |
| $\Delta G$ (kJ/mol) | −34.14 | 1.40 | −41.46 | 2.1 | −38.27 | 1.78 |
| Ka (M$^{-1}$) | 1.68E+06 | 9.3E+05 | 3.279E+07 | 1.4E+05 | 8.65E+06 | 2.9E+05 |
| No. of r-hGV/µm$^2$ of nanoparticles | 5.06E+04 | — | 1.20E+04 | — | 2.00E+04 | — |

TABLE VII

The molar enthalpy change (ΔH) of rhGH adsorbed to negatively charged. PLGA 5050 1A at 15° C. and 25° C. and its associated molar heat capacity change (ΔadsCp) in 10 mM buffer as a function of pH.

| pH | ΔH (kJ/mol) At 25° C. | ΔH (kJ/mol) At 15° C. | ΔCp (kJ/mol-K) |
|---|---|---|---|
| 7.2 | −94.2 | −18.29 | −7.591 |
| 5.3 | 363.25 | 52.21 | 31.104 |
| 4.0 | 110.5 | −56.36 | 16.686 |

It was concluded from the results of ITC studies that r-hGH adsorption is dependent upon the pH of the solution and exhibits differences in adsorption behavior onto different grades of PLGA polymer, depending on the surface hydrophobicity. r-hGH interaction with PLGA 5050 1A and PLGA 8515 3CE nanoparticles at pH 7.2 shows exothermic reaction and not a classical hydrophobic effect, while n is higher with 8515 3CE nanoparticles. The reaction with 5050 1A nanoparticles at pH 5.3 and 4.0 and 5050 E nanoparticles at pH 7.2 is endothermic and entropically driven indicating potential structural changes. Agreement of this ITC study results with work using techniques such as fluorescence spectroscopy, circular dichroism and dynamic light scattering, further demonstrates the suitability of PLGA 5050 1A and 8515 E for sustained delivery of r-hGH.

Enumerated Embodiments

The following enumerated embodiments are provided, the numbering of which is not to be construed as designating levels of importance:

Embodiment 1 provides a method of forming polypeptide-adsorbed poly(lactic-co-glycolic acid) (PLGA) particles, the method comprising contacting an aqueous suspension comprising PLGA particles with an aqueous solution comprising the polypeptide, wherein the PLGA particles comprise: (a) nanoparticles having a diameter of about 1 nm to about 100 nm; or (b) microparticles having size of about 0.5 μm to about 5 μm; or (c) porous microparticles having diameter of about 10 μm to about 20 μm and an aerodynamic diameter of about 0.5 μm to about 5 μm; wherein the aqueous solution comprises about 0.001 mg/ml to about 0.2 mg/ml of the polypeptide.

Embodiment 2 provides the method of Embodiment 1, wherein the polypeptide is selected from the group consisting of a monoclonal antibody, coagulation factor, enzyme, fusion protein, hormone, growth factor, and plasma protein.

Embodiment 3 provides the method of any of Embodiments 1-2, wherein the polypeptide is selected form the group consisting of human growth hormone (hGH), insulin, somatostatin analogue, recombinant human glucocerebrosidase, vasopressin, leuprolide acetate, goserelin acetate, triptorelin, GLP-I receptor agonist, coagulation factor IX, and recombinant factor VIII.

Embodiment 4 provides the method of any of Embodiments 1-3, wherein the aqueous suspension and the aqueous solution independently have a pH of about 6.5 to about 7.5.

Embodiment 5 provides the method of any of Embodiments 1-4, wherein the PLGA particles comprise a lactic acid/glycolic acid ratio from about 1:1 to about 6:1.

Embodiment 6 provides the method of any of Embodiments 1-5, wherein the PLGA particles comprise PLGA 5050 or PLGA 8515.

Embodiment 7 provides the method of any of Embodiments 1-6, wherein the PLGA particles comprise a PLGA polymer having a molecular weight from about 10 kDa to about 50 kDa.

Embodiment 8 provides the method of any of Embodiments 1-7, wherein at least a portion of the PLGA particles comprises an ester end-capped PLGA polymer.

Embodiment 9 provides the method of any of Embodiments 1-8, wherein the aqueous suspension is buffered.

Embodiment 10 provides the method of any of Embodiments 1-9, wherein the aqueous solution is buffered.

Embodiment 11 provides a composition comprising polypeptide-adsorbed PLGA particles formed through the method of any of Embodiments 1-10.

Embodiment 12 provides a composition comprising poly (lactic-co-glycolic acid) (PLGA) particles and a polypeptide; wherein the polypeptide is adsorbed on at least a fraction of the surface of the PLGA particles; wherein the PLGA particles comprise: nanoparticles having a diameter of about 1 nm to about 100 nm; microparticles having size of about 0.5 μm to about 5 μm; or porous microparticles having diameter of about 10 μm to about 20 μm and an aerodynamic diameter of about 0.5 μm to about 5 μm; wherein the PLGA particles comprise a lactic acid-to-glycolic acid ratio from about 1:1 to about 6:1; and wherein the PLGA particles comprise a PLGA polymer having a molecular weight from about 10 kDa to about 50 kDa;

Embodiment 13 provides a composition of any of Embodiments 11-12, wherein the polypeptide is selected from the group consisting of monoclonal antibody, coagulation factor, enzyme, fusion protein, hormone, growth factor, and plasma protein.

Embodiment 14 provides a composition of any of Embodiments 11-13, wherein the polypeptide is selected from the group consisting of human growth hormone (hGH), insulin, somatostatin analogue, recombinant human glucocerebrosidase, vasopressin, leuprolide acetate, goserelin acetate, triptorelin, GLP-I receptor agonist, coagulation factor IX, and recombinant factor VIII.

Embodiment 15 provides a composition of any of Embodiments 11-14, wherein the polypeptide is recombinant.

Embodiment 16 provides a composition of any of Embodiments 11-15, wherein the PLGA particles comprise an ester end-capped PLGA polymer.

Embodiment 17 provides a composition of any of Embodiments 11-16, wherein at least a portion of the polypeptide adsorbed to the surface of the PLGA particles retains its active secondary and tertiary structure as compared to the free non-adsorbed polypeptide.

Embodiment 18 provides a composition of any of Embodiments 11-17, wherein at least a portion of the polypeptide adsorbed to the surface of the PLGA particles is not significantly denatured by the adsorption process.

Embodiment 19 provides a composition of any of Embodiments 11-18, wherein the polypeptide adsorbs to the surface of the PLGA particles to form a monolayer.

Embodiment 20 provides a composition of any of Embodiments 11-19, wherein the polypeptide adsorbs to the surface of the PLGA particles to form more than one layer.

Embodiment 21 provides a composition of any of Embodiments 11-20, wherein the polypeptide is not imbedded in the PLGA particles.

Embodiment 22 provides a composition of any of Embodiments 11-21, wherein the composition comprises a (w/w) ratio of the polypeptide:PLGA of about 1:0.15 to about 1:6.

Embodiment 23 provides a composition of any of Embodiments 11-22, wherein the PLGA particles are biocompatible.

Embodiment 24 provides a composition of any of Embodiments 11-23, wherein the PLGA particles are biodegradable.

Embodiment 25 provides a composition of any of Embodiments 11-24, further comprising at least one pharmaceutically acceptable carrier.

Embodiment 26 provides a method of treating human growth hormone deficiency in a subject in need thereof, the method comprising administering to the subject a therapeutically effective amount of a composition of any of Embodiments 11-25, wherein the polypeptide comprises human growth hormone.

Embodiment 27 provides the method of Embodiment 26, wherein the human growth hormone is recombinant.

Embodiment 28 provides the method of any of Embodiments 26-27, wherein the subject is a mammal.

Embodiment 29 provides the method of any of Embodiments 26-28, wherein the mammal is a human.

Embodiment 30 provides a method of delivering a polypeptide to the lungs of a subject in need thereof, the method comprising administering to the lungs of the subject a therapeutically effective amount of the composition of any of Embodiments 11-25.

Embodiment 31 provides the method of Embodiment 30, wherein the subject is a mammal.

Embodiment 32 provides the method of any of Embodiments 30-31, wherein the mammal is a human.

The disclosures of each and every patent, patent application, and publication cited herein are hereby incorporated herein by reference in their entirety. While this invention has been disclosed with reference to specific embodiments, it is apparent that other embodiments and variations of this invention can be devised by others skilled in the art without departing from the true spirit and scope of the invention. The appended claims are intended to be construed to include all such embodiments and equivalent variations.

What is claimed is:

1. A method of forming polypeptide-adsorbed poly(lactic-co-glycolic acid) (PLGA) particles,
the method comprising contacting an aqueous suspension comprising PLGA particles with an aqueous solution comprising a polypeptide, whereby the polypeptide is adsorbed on the PLGA particles,
wherein the PLGA particles comprise nanoparticles having a diameter ranging from about 1 nm to about 100 nm;
wherein the PLGA particles comprise a lactic acid-to-glycolic acid ratio from about 1:1 to about 6:1;
wherein the PLGA particles comprise a PLGA polymer having a molecular weight from about 10 kDa to about 50 kDa;
wherein the aqueous solution comprises about 0.001 mg/ml to about 0.2 mg/ml of the polypeptide;
wherein at least a portion of the PLGA particles comprises an ester end-capped PLGA polymer;
wherein the polypeptide comprises a human growth hormone; and
wherein at least a portion of the human growth hormone adsorbed to the surface of the PLGA particles retains its active secondary and tertiary structure as compared to the polypeptide prior to adsorption, and is not significantly denatured by the adsorption process.

2. The method of claim 1, wherein the human growth hormone comprises a recombinant human growth hormone.

3. The method of claim 1, wherein the aqueous suspension and the aqueous solution independently have a pH of about 6.5 to about 7.5.

4. The method of claim 1, wherein the PLGA particles comprise PLGA 5050 or PLGA 8515.

5. The method of claim 1, wherein at least one of the aqueous suspension and the aqueous solution is buffered.

6. The method of claim 1, wherein the PLGA particles are selected from the group consisting of PLGA 5050 1A particles, PLGA 5050 5E particles, and PLGA 8515 3CE particles.

7. A composition comprising poly(lactic-co-glycolic acid) (PLGA) particles and a polypeptide;
wherein the polypeptide is adsorbed on at least a fraction of the surface of the PLGA particles;
wherein the PLGA particles comprise nanoparticles having a diameter of about 1 nm to about 100 nm;
wherein the PLGA particles comprise a lactic acid-to-glycolic acid ratio from about 1:1 to about 6:1;
wherein the PLGA particles comprise a PLGA polymer having a molecular weight from about 10 kDa to about 50 kDa;
wherein the PLGA particles comprise an ester end-capped PLGA polymer;
wherein the polypeptide comprises a human growth hormone; and
wherein at least a portion of the human growth hormone adsorbed to the surface of the PLGA particles retains its active secondary and tertiary structure as compared to the polypeptide prior to adsorption, and is not significantly denatured by the adsorption process.

8. The composition of claim 7, wherein the human growth hormone comprises a recombinant human growth hormone.

9. The composition of claim 7, wherein the polypeptide adsorbs to the surface of the PLGA particles to form a monolayer or more than one layer.

10. The composition of claim 7, wherein the polypeptide is not imbedded in the PLGA particles.

11. The composition of claim 7, wherein the composition comprises a (w/w) ratio of the polypeptide: PLGA of about 1:0.15 to about 1:6.

12. The composition of claim 7, wherein the PLGA particles are biocompatible or biodegradable.

13. The composition of claim 7, further comprising at least one pharmaceutically acceptable carrier.

14. The composition of claim 7, wherein the PLGA particles are selected from the group consisting of PLGA 5050 1A particles, PLGA 5050 5E particles, and PLGA 8515 3CE particles.

15. A method of treating human growth hormone deficiency in a subject in need thereof, the method comprising administering to the subject a therapeutically effective amount of a composition of claim 7.

16. The method of claim 15, wherein the human growth hormone is recombinant.

17. A method of delivering a polypeptide to a lung or pair of lungs of a subject in need thereof, the method comprising administering to the lung(s) of the subject a therapeutically effective amount of the composition of claim 7.

* * * * *